(12) United States Patent
Cid-Núñez et al.

(10) Patent No.: US 8,022,102 B2
(45) Date of Patent: Sep. 20, 2011

(54) UNSATURATED TETRACYCLIC TETRAHYDROFURAN DERIVATIVES

(75) Inventors: José Maria Cid-Núñez, Toledo (ES); Antonius Adrianus Hendrikus Petrus Megens, Beerse (BE); Andrés Avelino Trabanco-Suárez, Toledo (ES)

(73) Assignee: Janssen Pharmaceutica, NV (BE)

( * ) Notice: Subject to any disclaimer, the term of this patent is extended or adjusted under 35 U.S.C. 154(b) by 1164 days.

(21) Appl. No.: 11/571,090

(22) PCT Filed: Jun. 21, 2005

(86) PCT No.: PCT/EP2005/052891
§ 371 (c)(1),
(2), (4) Date: Dec. 21, 2006

(87) PCT Pub. No.: WO2006/000555
PCT Pub. Date: Jan. 5, 2006

(65) Prior Publication Data
US 2007/0191469 A1    Aug. 16, 2007

(30) Foreign Application Priority Data
Jun. 23, 2004    (EP) ........................ PCT/EP04/051204

(51) Int. Cl.
*A61K 31/343*    (2006.01)
*C07D 307/93*    (2006.01)
(52) U.S. Cl. ........ 514/468; 514/285; 514/410; 514/443; 546/62; 548/418; 549/31; 549/457
(58) Field of Classification Search .................... 549/32, 549/439, 440, 443, 31, 457; 546/62; 548/418; 514/285, 410, 443, 468
See application file for complete search history.

(56) References Cited

U.S. PATENT DOCUMENTS
6,511,976 B1 * 1/2003 Andres-Gil et al. ....... 514/232.8

FOREIGN PATENT DOCUMENTS
WO    99/19317 A1    10/1997
WO    97/38991 A1    4/1999

OTHER PUBLICATIONS
International Search Report, PCT/EP2005/052891, dated Mar. 13, 2006, 12 pages.

* cited by examiner

*Primary Examiner* — Bernard Dentz

(57) ABSTRACT

This invention concerns novel substituted unsaturated tetracyclic tetrahydrofuran derivatives with binding affinities towards serotonine receptors, in particular 5-$HT_{2A}$ and 5-$HT_{2C}$ receptors, and towards dopamine receptors, in particular dopamine D2 receptors and with norepinephrine reuptake inhibition properties, pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.

The compounds according to the invention can be represented by general Formula (I)

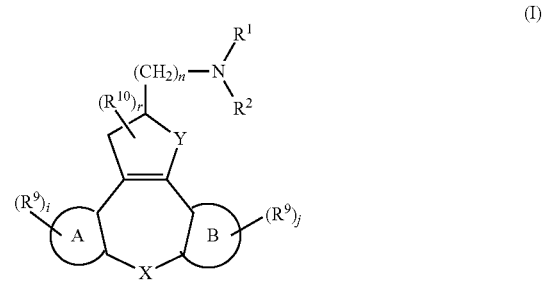

and comprises also the pharmaceutically acceptable acid or base addition salts thereof, the stereochemically isomeric forms thereof, the N-oxide form thereof and prodrugs thereof, wherein all substitutents are defined as in Claim 1.

5 Claims, No Drawings

UNSATURATED TETRACYCLIC TETRAHYDROFURAN DERIVATIVES

This application is a National Stage application under 35 U.S.C. 371 of PCT Application No. PCT/EP2005/052891 filed 21 Jun. 2005, which claims priority from PCT Application No. PCT/EP2004/051204 filed 23 Jun. 2004, the contents of all of which are hereby incorporated by reference.

FIELD OF THE INVENTION

This invention concerns novel substituted unsaturated tetracyclic tetrahydrofuran derivatives with binding affinities towards serotonin receptors, in particular 5-$HT_{2A}$ and 5-$HT_{2C}$ receptors, and towards dopamine receptors, in particular dopamine D2 receptors and with norepinephrine reuptake inhibition properties, pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.

BACKGROUND PRIOR ART

WO 97/38991, published Oct. 23, 1997 (Janssen Pharmaceutica N.V.) discloses substituted tetracyclic tetrahydrofuran derivatives that may be used as therapeutic agents in the treatment or prevention of CNS disorders, cardiovascular disorders or gastrointestinal disorders. In particular, the compounds show affinity for the serotonin 5-$HT_2$ receptors, particularly for the 5-$HT_{2A}$ and 5-$HT_{2C}$-receptors.

WO 99/19317, published Apr. 22, 1999 (Janssen Pharmaceutica N.V.) discloses substituted tetracyclic tetrahydrofuran derivatives with a specific halogen substitution pattern on the dibenzoazepine, dibenzooxepine, dibenzothiepine or dibenzosuberane ring. The compounds are useful in the treatment or prevention of CNS disorders, cardiovascular disorders or gastrointestinal disorders and show a faster onset of action over the compounds as disclosed in WO 97/38991.

Both WO 03/048146, published Jun. 12, 2003 (Janssen Pharmaceutica N.V.) and WO 03/048147, published Jun. 12, 2003 (Janssen Pharmaceutica N.V.) disclose processes for the preparation of each of the 4 diastereomers of cis-, respectively trans-fused 3,3a,8,12b-tetrahydro-2H-dibenzo[3,4:6,7]cyclohepta[1,2-b]furan derivatives in a stereochemically pure form from a single enantiomerically pure precursor. The compounds show affinity for the serotonin 5-$HT_{2A}$, 5-$HT_{2C}$ and 5-$HT_7$ receptors and the $H_1$-receptors ($pIC_{50}$=7.15-7.89), D2 and/or D3 receptors and for the norepinephrine reuptake transporters ($pIC_{50}$=6.01-7.34).

WO 03/040122, published May 15, 2003 (Janssen Pharmaceutica N.V.) discloses mandelate salts of the compounds according to WO 97/38991 and WO 99/19317. Said salts were surprisingly found to be more stable at enhanced temperature and relative humidity than the compounds disclosed in WO 97/38991 and WO 99/19317.

Since the compounds of WO 97/38991 and WO 99/19317 exist as 8 stereoisomers, each with a different pharmacological profile, the yield of their production process is very low.

DESCRIPTION OF THE INVENTION

It is the object of the present invention to provide novel analogues of the tetracyclic tetrahydrofuran derivatives of WO 97/38991 and WO 99/19317, which are easier to synthesize and the synthesis of which has a higher yield, yet which have a similar or even better profile than the compounds disclosed in WO 97/38991 and WO 99/19317.

This goal is achieved by the present novel compounds according to Formula (I)

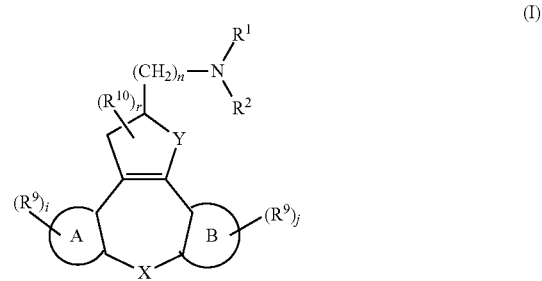

(I)

the pharmaceutically acceptable acid or base addition salts thereof, the stereochemically isomeric forms thereof, the N-oxide form thereof and prodrugs thereof, wherein:

n is an integer, equal to zero, 1, 2, 3, 4, 5 or 6;

i, j are integers, independently from each other, equal to zero, 1, 2, 3 or 4;

r is an integer, equal to zero, 1, 2 or 3

$R^1$ and $R^2$ are, each independently from each other, selected from the group of hydrogen; alkyl; alkenyl; aryl; arylalkyl; arylalkenyl; alkyloxyalkyl; arylcarbonylalkyl; alkylcarbonyloxyalkyl; alkyloxycarbonylalkyl; alkylcarbonyl; arylcarbonyl; arylalkylcarbonyl; alkyloxycarbonyl; aryloxycarbonyl; alkyloxycarbonylalkylcarbonyl; mono- or di(alkyl)aminocarbonyl; mono- or di(aryl)aminocarbonyl; mono- or di(arylalkyl)aminocarbonyl; aminocarbonylalkyl; mono- or di(alkyloxycarbonylalkyl)aminocarbonyl; mono- or di(alkyl)aminocarbonylalkyl; mono- or di(aryl)aminocarbonylalkyl; mono- or di(alkyl)aminocarbonylalkenyl; mono- or di(alkylsulphonyl)aminocarbonylalkyl; mono- or di(arylsulphonyl)aminocarbonylalkyl; alkylsulphonyl; arylsulphonyl; arylalkylsulphonyl; mono- or di(alkyl)aminothiocarbonyl; mono- or di(aryl)aminothiocarbonyl; mono- or di(arylalkyl)aminothiocarbonyl; mono-, di- or tri(alkyl)amidino; mono-, di- or tri(alkyl)amidinoalkyl; mono-, di- or tri(aryl)amidino and mono-, di- or tri(arylalkyl)amidino; pyrrolidinyl, optionally substituted with oxo; tetrazolylalkyl; or $R^1$ and $R^2$ taken together with the nitrogen atom to which they are attached may form a radical of Formula (a-1) to (a-7):

(a-1)

(a-2)

-continued

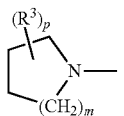
(a-3)

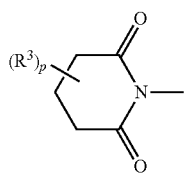
(a-4)

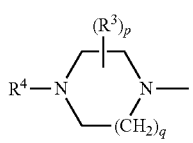
(a-5)

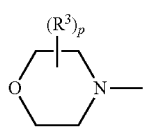
(a-6)

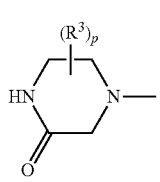
(a-7)

wherein:
p is an integer, equal to zero, 1, 2, 3 or 4;
q is an integer, equal to 1 or 2;
m is an integer, equal to zero, 1, 2 or 3;
each $R^3$ is, independently from each other, selected from the group of halo; hydroxy; alkyloxy; aryloxy; alkyl; aryl; alkylcarbonyl; alkyloxycarbonyl; arylcarbonyl; aryloxycarbonyl and mono- or di(alkyl)amino; or
two $R^3$-radicals may form together a bivalent radical of Formula —$CR^5R^5$—$CR^5R^5$—O—    (b-1);

—O—$CR^5R^5$—$CR^5R^5$—    (b-2);

—O—$CR^5R^5$—$CR^5R^5$—O—    (b-3);

—O—$CR^5R^5$—$CR^5R^5$—$CR^5R^5$—    (b-4);

—$CR^5R^5$—$CR^5R^5$—$CR^5R^5$—O—    (b-5);

—O—$CR^5R^5$—$CR^5R^5$—$CR^5R^5$—O—    (b-6);

—O—$CR^5R^5$—$CR^5R^5$—$CR^5R^5$—$CR^5R^5$—    (b-7);

—$CR^5R^5$—$CR^5R^5$—$CR^5R^5$—$CR^5R^5$—O—    (b-8); and

—O—$CR^5R^5$—$CR^5R^5$—$CR^5R^5$—O—    (b-9);

wherein $R^5$ is selected from the group of hydrogen; halo; hydroxy; alkyloxy and alkyl;
$R^4$ is selected from the group of hydrogen; alkyl; alkylcarbonyl; arylcarbonyl; alkyloxycarbonyl; aryloxycarbonyl; arylalkylcarbonyl; alkyloxycarbonylalkylcarbonyl; arylalkyl; alkyloxyalkyl; alkylcarbonyloxyalkyl; alkyloxycarbonylalkyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl; arylalkylsulphonyl; mono- or di(alkyl)aminothiocarbonyl; mono- or di(aryl)aminothiocarbonyl; mono- or di(arylalkyl)aminothiocarbonyl; mono-, di- or tri(alkyl)amidino; mono-, di- or tri(aryl)amidino and mono-, di- or tri(arylalkyl)amidino;

A and B are, each independently from each other, aryl or an heteroaryl radical selected from the group of furyl; thienyl; pyrrolyl; oxazolyl; thiazolyl; imidazolyl; isoxazolyl; isothiazolyl; oxadiazolyl; triazolyl; pyridinyl; pyridazinyl; pyrimidinyl; pyrazinyl; indolyl; indolizinyl; isoindolyl; benzofuryl; isobenzofuryl; benzothienyl; indazolyl; benzimidazolyl; benzthiazolyl; quinolizinyl; quinolinyl; isoquinolinyl; phthalazinyl; quinazolinyl, quinoxalinyl; chromenyl; naphthyridinyl and naphthalenyl;

each $R^9$ is, independently from each other, selected from the group of hydrogen; halo; cyano; hydroxy; carboxyl; nitro; amino; mono- or di(alkyl)amino; alkylcarbonylamino; aminosulfonyl; mono- or di(alkyl)aminosulfonyl; alkyl; alkenyl; alkyloxy; alkylcarbonyl and alkyloxycarbonyl;

$R^{10}$ is selected from the group of hydrogen; alkyl; halo and cyano;

Y is O; S; S(=O); S(=O)$_2$ or $NR^8$;

X is $CR^6R^7$; O; S; S(=O); S(=O)$_2$ or $NR^8$; wherein
$R^6$ and $R^7$ each independently from each other, are selected from the group of hydrogen; hydroxy; alkyl and alkyloxy; or
$R^6$ and $R^7$ taken together may form a radical selected from the group of methylene (=CH$_2$); mono- or di(cyano)methylene; a bivalent radical of Formula —(CH$_2$)$_2$—, —(CH$_2$)$_3$—, —(CH$_2$)$_4$—, —(CH$_2$)$_5$—, —O—(CH$_2$)$_2$—O—, —O—(CH$_2$)$_3$O—; or, together with the carbon atom to which they are attached, a carbonyl;

$R^8$ is selected from the group of hydrogen; alkyl; alkylcarbonyl; arylcarbonyl; arylalkyl; arylalkylcarbonyl; alkylsulfonyl; arylsulfonyl and arylalkylsulfonyl; aryl is phenyl, optionally substituted with 1, 2 or 3 substitutents independently from each other, selected from the group of halo, hydroxy, alkyloxy and alkyl;

alkyl is a straight or branched saturated hydrocarbon radical having from 1 to 6 carbon atoms; or a cyclic saturated hydrocarbon radical having from 3 to 6 carbon atoms; each radical optionally substituted with one or more radicals selected from the group of halo, cyano, oxo, hydroxy, formyl, carboxyl and amino;

alkenyl is a straight or branched unsaturated hydrocarbon radical having from 1 to 6 carbon atoms; or a cyclic unsaturated hydrocarbon radical having from 3 to 6 carbon atoms; each radical optionally substituted with one or more radicals selected from the group of halo, cyano, oxo, hydroxy, formyl, carboxyl or amino radicals; and halo is fluoro, chloro, bromo or iodo.

The present compounds differ structurally from the compounds of WO 97/38991 and WO 99/19317 by inter alia the presence of a double bond between carbon atoms 3a and 12b, thereby reducing the number of asymmetric centers from 3 to 1 and, thus, the number of possible enantiomers from 8 to 2. Consequently, the compounds of the present invention have a much simpler structure than the prior art compounds, which facilitates chemical synthesis enormously.

More in particular, the invention relates to a compound according to the general Formula (I), the pharmaceutically acceptable acid or base addition salts thereof, the stereochemically isomeric forms thereof, the N-oxide form thereof and a prodrug thereof, wherein:
  n is equal to or 2;
  i, j are, independently from each other, equal to zero or 1;
  r is equal to 0 or;
  $R^1$ and $R^2$ are, each independently from each other, hydrogen; alkyl; alkenyl; aryl; arylalkenyl; arylcarbonylalkyl; alkyloxycarbonylalkyl; aryloxycarbonyl; alkyloxycarbonylalkylcarbonyl; aminocarbonylalkyl; mono- or di(alkyl)aminocarbonylalyl; mono- or di(aryl)aminocarbonylalkyl; mono- or di(alkyl)aminocarbonylalkenyl; mono- or di(alkylsulphonyl)aminocarbonylalkyl; mono- or di(arylsulphonyl)aminocarbonylalkyl; alkylsulphonyl; mono-, di- or tri(alkyl)amidinoalkyl; pyrrolidinyl, optionally substituted with oxo; tetrazolylalkyl; or
  $R^1$ and $R^2$ taken together with the nitrogen atom to which they are attached may form a radical of Formula (a-1), (a-3), (a-5), (a-6) or (a-7) wherein:
    p is equal to zero, 1 or 2;
    q is equal to 1;
    m is equal to 1 or 2;
    each $R^3$ is, independently from each other, selected from the group of hydroxy; alkyloxy; alkyl; and mono- or di(alkyl)amino; or two $R^3$-radicals may form together a bivalent radical of Formula (b-3) wherein $R^1$ is hydrogen;
    $R^4$ is selected from the group of alkyl; alkylcarbonyl; arylcarbonyl; alkyloxycarbonyl; aryloxycarbonyl; arylalkylcarbonyl; alkyloxycarbonylalkylcarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl and arylalkylsulphonyl;
  A and B are, each independently from each other, aryl or an heteroaryl radical selected from the group of thienyl; pyridinyl and indolyl;
  each $R^9$ is, independently from each other, selected from the group of hydrogen; halo; cyano; alkyl and alkenyl;
  $R^{10}$ is hydrogen;
  Y is O;
  X is $CR^6R^7$, O, S or $NR^8$; wherein
    $R^6$ and $R^7$ each independently from each other are selected from the group of hydrogen and alkyl; or
    $R^6$ and $R^7$ taken together may form the radical methylene (=$CH_2$); or, together with the carbon atom to which they are attached, a carbonyl;
  $R^8$ is selected from the group of alkyl and arylalkyl;
  aryl is phenyl, optionally substituted with 1 substitutent selected from the group of halo, hydroxy, alkyloxy and alkyl;
  alkyl is a straight saturated hydrocarbon radical having from 1 to 6 carbon atoms, optionally substituted with one or more hydroxy, cyano or carboxyl radicals;
  alkenyl is a straight unsaturated hydrocarbon radical having from 1 to 6 carbon atoms; and
  halo is fluoro, chloro or bromo.
  More in particular, the invention relates to a compound according to the general Formula (I), the pharmaceutically acceptable acid or base addition salts thereof, the stereochemically isomeric forms thereof, the N-oxide form thereof and a prodrug thereof, wherein:
  n is equal to 1;
  i is equal to 0;
  j is equal to 1;
  r is equal to 0;
  $R^1$ and $R^2$ are, each independently from each other, hydrogen or methyl
  A and B are phenyl;
  $R^9$ is halo;
  $R^{10}$ is hydrogen;
  Y is O;
  X is $CH_2$ and
  halo is fluoro, chloro or bromo.

DETAILED DESCRIPTION OF THE INVENTION

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds according to the invention possess at least 1 oxydizable nitrogen (tertiary amines moiety). It is therefore highly likely that N-oxides are to form in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substitutents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center, R* and S* each indicate optically pure stereogenic centers with undetermined absolute configuration. If "α" and "β" are used: the position of the highest priority substituent on the asymmetric carbon atom in the ring system having the lowest ring number, is arbitrarily always in the "α" position of the mean plane determined by the ring system. The position of the highest priority substitutent on the other asymmetric carbon atom in the ring system (hydrogen atom in compounds according to Formula (I)) relative to the position of the highest priority substitutent on the reference atom is denominated "α", if it is on the same side of the mean plane determined by the ring system, or "β", if it is on the other side of the mean plane determined by the ring system.

The numbering of the tetracyclic ring-system present in the compounds of Formula (I) when A and B are phenyl, as defined by Chemical Abstracts nomenclature is shown below.

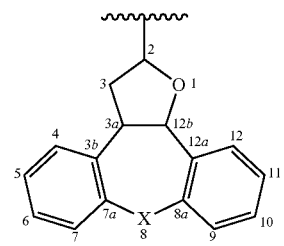

The compounds of Formula (I) have at least one asymmetric center at carbon atom 2. Said asymmetric center and any other asymmetric center, which may be present (e.g. at atom 8), are indicated by the descriptors R and S. When e.g. a monocyanomethylene moiety is present in the compounds of Formula (I) at position 8, said moiety may have the E- or Z-configuration.

The invention also comprises derivative compounds (usually called "pro-drugs") of the pharmacologically active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on prodrugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the Formula —COOR$^x$, where R$^x$ is a $C_{1-6}$alkyl, phenyl, benzyl or one of the following groups:

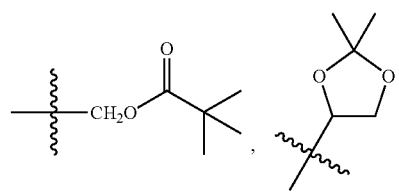

Amidated groups include groups of the Formula —CONR$^y$R$^z$, wherein R$^y$ is H, $C_{1-6}$allyl, phenyl or benzyl and R$^z$ is —OH, H, $C_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

The compounds of the present invention show affinity for $5\text{-}HT_2$ receptors, particularly for $5\text{-}HT_{2A}$ and $5\text{-}HT_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden) and affinity for the D2 receptor as well as norepinephrine reuptake inhibition activity. The serotonin antagonistic properties of the present compounds may be demonstrated by their inhibitory effect in the "5-hydroxytryptophan Test on Rats" which is described in Drug Dev. Res., 13, 237-244 (1988).

The compounds of the present invention also have favourable physicochemical properties. For instance, they are chemically stable compounds.

In view of their capability to block $5\text{-}HT_2$ receptors, and in particular to block $5\text{-}HT_{2A}$ and $5\text{-}HT_{2C}$ receptors, as well as the D2 receptor and by also effecting the norepinephrine reuptake inhibition activity, the compounds according to the invention are useful as a medicine, in particular in the prophylactic and therapeutic treatment of conditions mediated through either of these receptors.

The invention therefore relates to a compound according to the general Formula (I), the pharmaceutically acceptable acid or base addition salts thereof the stereochemically isomeric forms thereof, the N-oxide form thereof and prodrugs thereof, for use as a medicine.

The invention also relates to the use of a compound according to the general Formula (I), the pharmaceutically acceptable acid or base addition salts thereof, the stereochemically isomeric forms thereof, the N-oxide form thereof and prodrugs thereof for the manufacture of a medicament for treating, either prophylactic or therapeutic or both, conditions mediated through the $5\text{-}HT_2$, and D2 receptor, as well as the through norepinephrine reuptake inhibition.

In view of these pharmacological and physicochemical properties, the compounds of Formula (I) are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children such as ADHD, aggression, memory disorders and attitude disorders in older people, addiction, obesity, bulimia and similar disorders. In particular, the present compounds may be used as anxiolytics, antidepressants, antipsychotics, anti-schizophrenia agents, antimigraine agents and as agents having the potential to overrule the addictive properties of drugs of abuse.

The compounds of Formula (I) may also be used as therapeutic agents in the treatment of motoric disorders. It may be advantageous to use the present compounds in combination with classical therapeutic agents for such disorders.

The compounds of Formula (I) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of Formula (I), it follows that the present invention also provides a method of treating warm-blooded animals suffering from such diseases, said method comprising the systemic administration of a therapeutic amount of a compound of Formula (I) effective in treating the above described disorders, in particular, in treating anxiety, psychosis, depression, migraine and addictive properties of drugs of abuse.

The present invention thus also relates to compounds of Formula (I) as defined hereinabove for use as a medicine, in particular, the compounds of Formula (I) may be used for the manufacture of a medicament for treating anxiety, psychosis, depression, migraine and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a prodrug thereof.

The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be Formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to Formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

The following examples are intended to illustrate and not to limit the scope of the present invention.

Preparation

Suitable preparation schemes for the compounds of the invention are the following:

Scheme A

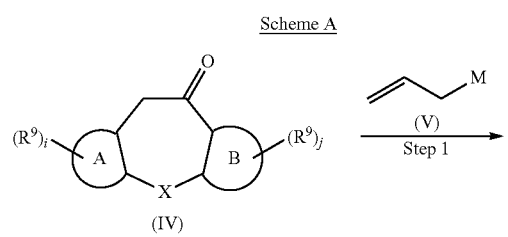

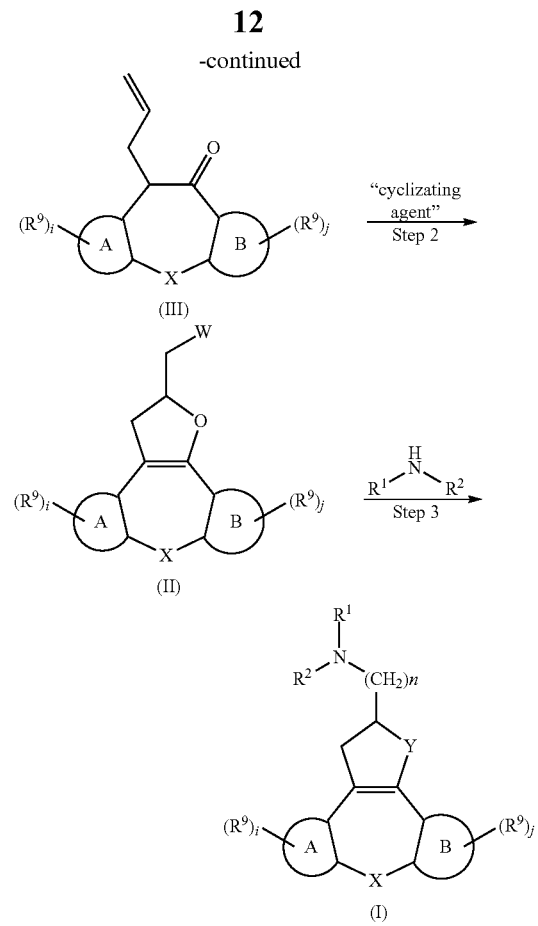

Step 1: Reaction of an intermediate compound of Formula (IV) with a reagent of Formula (V). This reaction can be done by any one of the art-known procedures for alkylation of ketones in position α under acidic or basic reaction conditions (for example the reaction can be done in an organic solvent such as, for example, dichloromethane, with a base such as, for example, lithium diisopropylamine and using allyl bromide as the alkylating agent) and yields an intermediate compound of Formula (III) wherein $R^9$, i, j, ring A, ring B and X all have the meaning as described above for a final compound of Formula (I). For a compound of Formula (V), M is a suitable group for an alkylation reaction, such as, for example halo, hydroxy or acetoxy.

Alternatively an intermediate of Formula (III) can be obtained via a Claisen rearrangement by heating an intermediate of Formula (IIIa), for example at 220° C., in an organic solvent such as toluene. Intermediates of Formula (IIIa) can be prepared by an O-allylation reaction of an intermediate of Formula (IV) with allylbromide, in an organic solvent such as DMF, in the presence of a suitable base such as, for example, potassium carbonate. The reaction is best conducted at elevated temperatures such as, for example, 60° C.

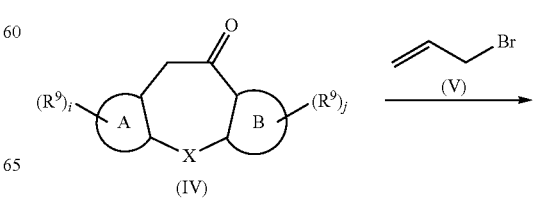

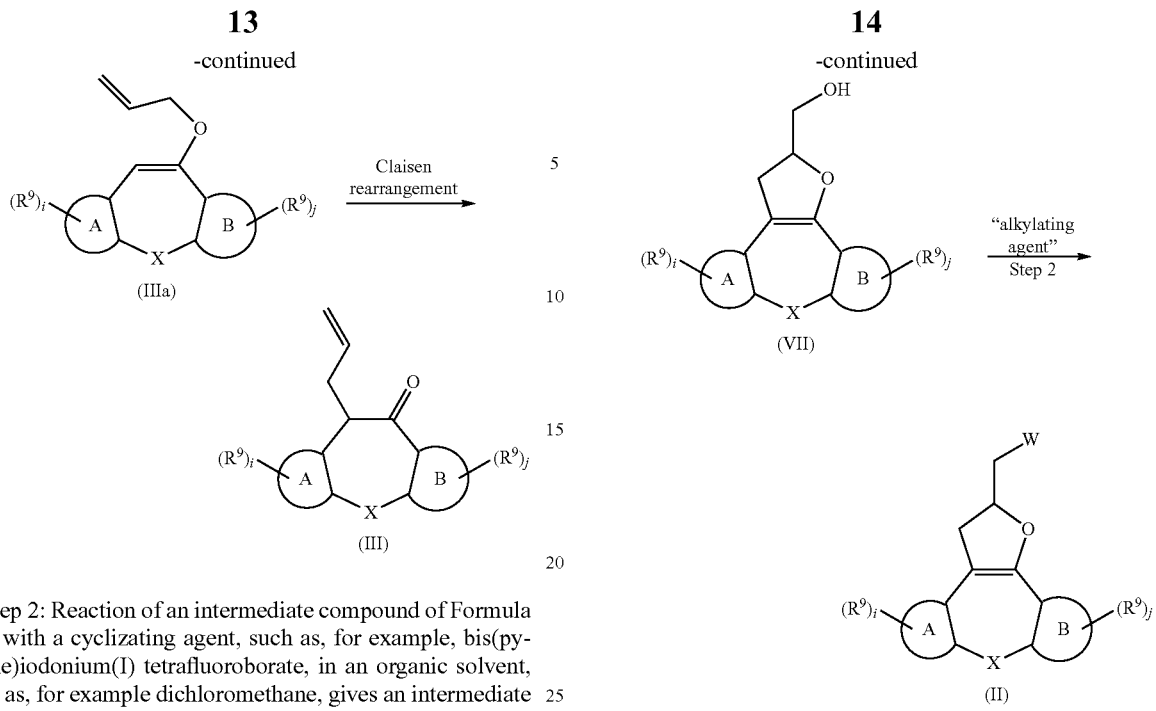

Step 2: Reaction of an intermediate compound of Formula (III) with a cyclizating agent, such as, for example, bis(pyridine)iodonium(I) tetrafluoroborate, in an organic solvent, such as, for example dichloromethane, gives an intermediate compound of Formula (II) wherein W represents a suitable leaving group, preferably a halo, alkyl- or arylsulphonyloxy-, in particular 4-(methylphenyl)sulphonyloxy- or iodo. An intermediate compound of Formula (II) wherein $R^9$, i j, ring A, ring B and X all have the meaning as described above for a final compound of Formula (I), and wherein W represents said leaving group, is new.

Step 3: N-alkylation of an intermediate compound of Formula (II) with an amine of Formula $HNR^1R^2$, wherein $R^1$ and $R^2$ are defined as in Formula (I), by any of the art-known procedures gives a final compound of Formula (I). For instance, said N-alkylation can conveniently be carried out as described in WO 97/38991 in a reaction-inert solvent such as, for example, methanol, methylisobutyl ketone, N,N-dimethylformamide or dimethylsulfoxide, and optionally in the presence of a suitable base. Stirring and elevated temperatures, for instance reflux temperature, may enhance the rate of the reaction. Typical reaction conditions are 8 hours at 130° C.

Alternatively, said N-alkylation may also be performed using the procedure described by Monkovic et al. (J. Med. Chem. (1973), 16(4), p. 403-407) which involves the use of a pressurised reaction vessel.

Alternatively, said N-alkylation may also be performed by heating at high temperature, for example 120° C., an intermediate of Formula (II), an amine of Formula $NHR^1R^2$ and a base, for example calcium oxide, in an organic solvent such as THF, in a pressurised reaction vessel.

Step 1: Cyclization of an intermediate compound of Formula (VI) (which can be prepared according to WO 03/048146 and WO 03/048147) in an acidic reaction media, such as, for example, hydrochloric acid in isopropyl alcohol, gives an intermediate compound of Formula (VI) wherein $R^9$, i, j, ring A, ring B and X all have the meaning as described above for a final compound of Formula (I).

Step 2: O-alkylation of an intermediate compound of Formula (VII) with a suitable alkylating agent, such as, for example, 4-(methylphenyl)sulphonylchloride, by any of the art-known procedures gives an intermediate compound of Formula (II) which is new. This intermediate compound can be treated, for example, as in Step (3) for Route A, yielding a final compound of Formula (I).

Scheme C

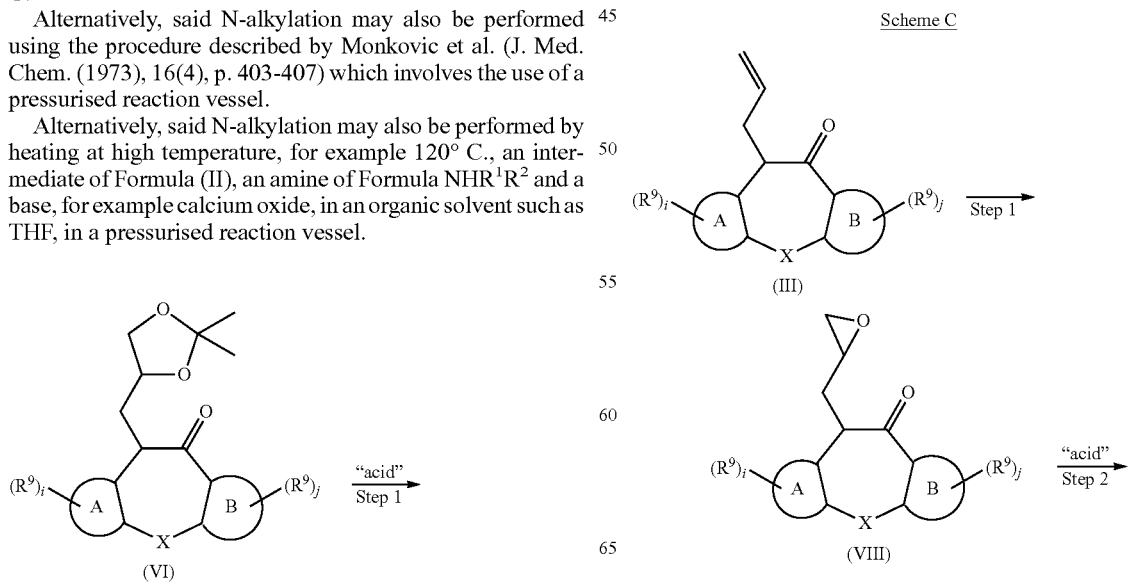

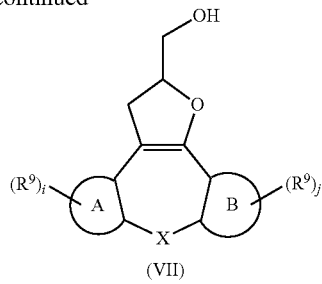

(VII)

Step 1: Epoxydation of the double bond of an intermediate compound of Formula (III) by any of the art-known procedures, such as, for instance, using 3-chloroperbenzoic acid, in an inert solvent such as, for example, dichloromethane, yields an intermediate compound of Formula (VIII). Typical reaction conditions are stirring at room temperature for 8 hours. An intermediate compound of Formula (VIII), wherein $R^9$, i j, ring A, ring B and X have the meaning as described above for a final compound of Formula (I), is new.

Step 2: Rearrangement of an intermediate compound of Formula (VIII) under acidic conditions, such as, for example, Amberlyst 15, in an inert solvent such as, for example, dichloromethane, yields an intermediate compound of Formula (VII). This intermediate compound can be treated, for example, as in Step (2) for Route B, yielding a final compound of Formula (II) which can be treated, for example, as in Step (3) for Route A, yielding a compound of Formula (I).

Scheme D

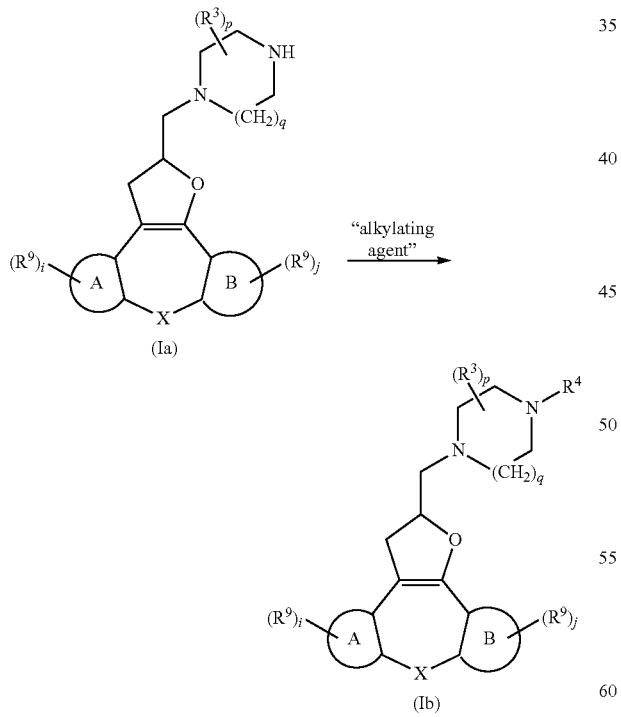

A final compound of Formula (Ib) wherein $R^9$, i, j, ring A, ring B, X, $R^3$, $R^4$, p and q all have the meaning as described above, can be prepared by reaction of a compound of Formula (Ia) (prepared by any of the preparation routes A, B, C as mentioned above) with a suitable alkylating agent, such as an acid halide-, isocyanate-, sulphonychloride derivatives, by any of the art-known procedures (such as, for example, in the presence of a suitable base such as polymer bound supported diisopropylethylamine, in an inert solvent such as, for example, dichloromethane).

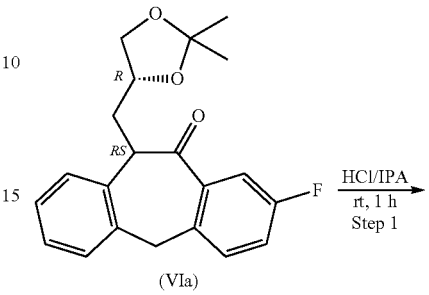

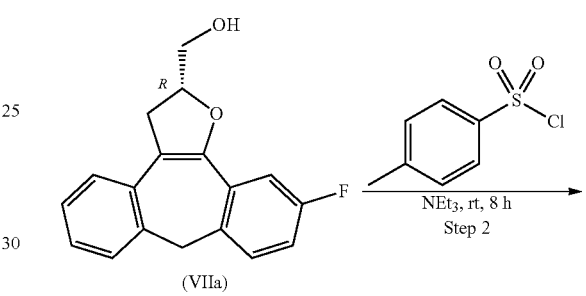

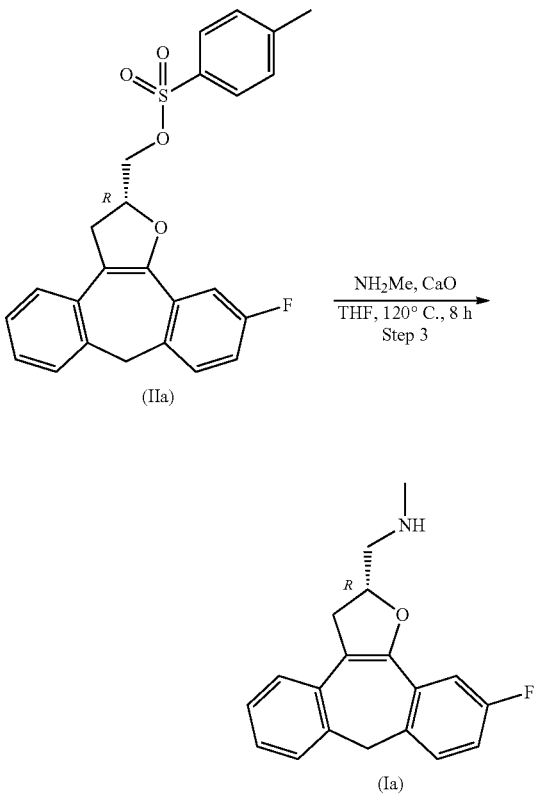

A preparation route for compound 3 with Formula (Ia) is shown in the above scheme. Synthesis of the intermediate (VIa) is described in WO 03/049146 A1, which is included herein by reference.

Step 1: The same procedure described in Step 1 for route B. Cyclization of an intermediate of Formula (VIa) in an acidic reaction media, such as, for example hydrochloric acid in isopropylic alcohol at room temperature gives an intermediate compound of Formula (VIIa), which is novel.

Step 2: The same procedure described in step 2 of Route B. O-Alkylation of an intermediate compound of Formula (VIIa) with a suitable alkylating agent such as for example 4-(methylphenyl)sulphonyl chloride, by any of the art known procedures, gives an intermediate compound of Formula (IIa), which is new.

Step 3: This intermediate of Formula (IIa) can be treated, for example as in step 3 for route A, with an amine such as, for example methylamine, and a base such as, for example CaO, in an organic solvent such as, for example THF, at high temperatures, for example 120° C., in pressurised reaction vessel for 8 hours, yielding a final compound of Formula (Ia), which is novel.

Pure stereochemically isomeric forms of the compounds of Formula (I) may be obtained by the application of art-known procedures. Diastereomers may be separated by physical methods such as selective crystallization and chromatographic techniques, e.g. counter-current distribution, liquid chromatography and the like.

The compounds of Formula (I) as prepared in the hereinabove described processes are generally racemic mixtures of enantiomers which can be separated from one another following art-known resolution procedures. The racemic compounds of Formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

EXPERIMENTAL PART

A. Preparation of the Intermediate Compounds

Hereinafter "RT" means room temperature, "HATU" means 1H-1,2,3-triazolo[4,5-b]pyridinium3-oxide, 1-[bis(dimethylamino)methylene]hexafluorophoshate, "THF" means tetrahydrofuran, "MTBE" means tert-butyl methyl ester, "DMAP" means 4-dimethylaminopyridine, "DIPEA" means diisopropylethylamine, "DIPE" means diisopropylether and "DMF" means N,N-dimethylformamide.

Example A1 a1. Preparation of Intermediate Compound 19

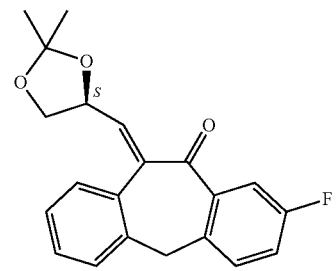

A solution of 2,2-dimethyl-1,3-dioxane-4-carboxaldehyde (6.5 g; 0.050 mol) in THF (20 mL) was added slowly to a stirred solution of

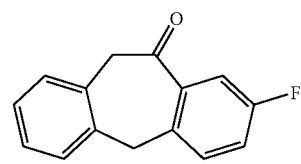

((prepared according to teachings in WO03/048146 A1, of which the content is herein included) (8.7 g; 0.038 mol) in THF (40 mL) at 20° C. under $N_2$-flow. Subsequently, anhydrous $MgCl_2$ (4.94 g) and potassium tert-butoxide (0.75 g) were added at 20° C. After stirring for 22 hours at 20-25° C., HCl cp (1.3 mL) in $H_2O$ (69 mL) was added dropwise maintaining the temperature between 20 and 25° C. After 10 minutes of stirring, the organic layer was separated and the solvent evaporated to obtain 6.6 g of intermediate compound 19 (92%).

a2. Preparation of Intermediate Compound 20

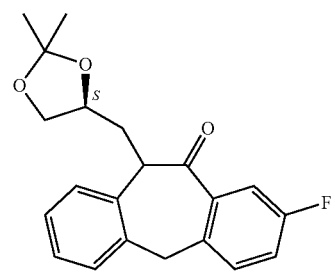

A mixture of intermediate compound 19 (15 g; 0.044 mol), Pd/C 10% (1 g), MeOH (100 mL) was hydrogenated at 40 psi and rt for 16 hours. Then the catalyst was filtered off through celite. The filtrated was collected and the solvent was evaporated under reduced pressure to obtain 13 g of intermediate compound 20 (86%).

a3. Preparation of Intermediate Compound 1

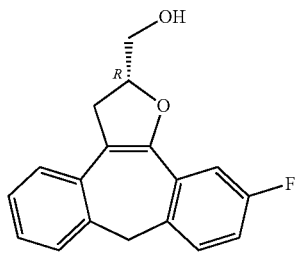

A mixture of

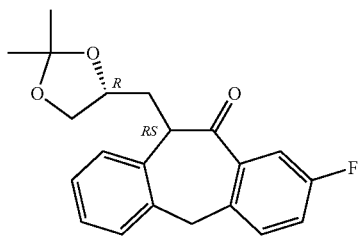

(prepared according to teachings in WO03/048146 A1, of which the content is herein included) (350 g; 1.028 mol), HCl (340 mL), H₂O (1.83 L) and THF (1.83 L) was stirred at room temperature overnight. Subsequently, the reaction mixture was extracted with toluene (2×2 L), the combined organic layers were washed with 1 N NaHCO₃/H₂O-solution (4 L) and dried over MgSO₄. After evaporation of the solvent under reduced pressure, the residue was redissolved in DIPE (980 mL) and refluxed until a clear solution was obtained. The solution was cooled to 40° C., seeded and further cooled to room temperature while stirring overnight. The precipitate was filtered off and dried under reduced pressure overnight at 45° C. Yield: 198 g of intermediate compound 1 (68%).

a4. Preparation of Intermediate Compound 11

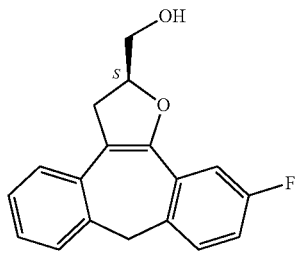

A mixture of intermediate compound 20 (0.0499 mol) in HCl/2-propanol (100 mL) and 2-propanol (250 mL) was stirred for 1.5 hours at room temperature. The solvent was evaporated under reduced pressure. The residue as dissolved in CH₂Cl₂ (300 mL). The organic solution was washed with an aqueous NaHCO₃ solution (3×200 mL), water (2×200 mL), and brine (2×100 mL), then dried (Na₂SO₄), filtered and the solvent was evaporated. Yield: 14 g of intermediate compound 11 (99%).

b1. Preparation of Intermediate Compound 2

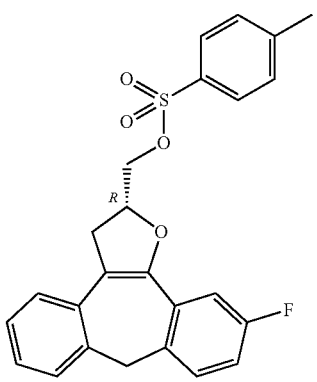

To a stirred mixture of intermediate compound 1 (320 g; 1.134 mol), Et₃N (253 g; 2.5 mol) and CH₂Cl₂ (4.8 L), DMAP (144 g; 1.18 mol) and 4-(methylphenyl)sulphonyl chloride (480 g; 2.5 mol) were added at room temperature. After stirring overnight at room temperature, the reaction mixture was washed twice with 3 L H₂O, dried over MgSO₄ and concentrated under vacuum. The residue was redissolved in 2.3 L of iPrOH and 1.4 L of toluene and refluxed until a clear solution was obtained. The solution was cooled to 30° C., seeded and further cooled to room temperature while stirring overnight. The precipitate was filtered off and dried under reduced pressure overnight at 45° C. Yield: 312 g of intermediate compound 2 (63%).

b2. Preparation of Intermediate Compound 12

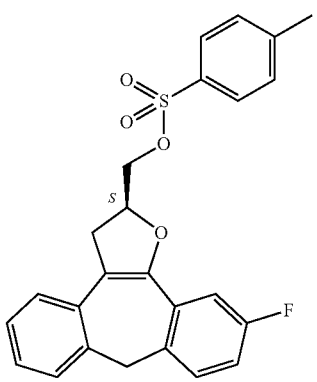

A mixture of intermediate compound 11 prepared according to A1.a4) (0.0496 mol) and Et₃N (0.0496 mol) in CH₂Cl₂, dry (500 mL) was stirred for 15 minutes at room temperature. The reaction mixture was washed with an aqueous NH₄Cl solution (2×100 mL), 1 N HCl (2×200 mL), an aqueous NaHCO₃ solution (2×200 mL) and brine (2×200 mL). The organic layer was separated, dried (Na₂SO₄), filtered and the solvent was evaporated. The residue was purified by short open column chromatography over silica gel (eluent: heptane/EtOAc 6/4). The product fractions were collected and the solvent was evaporated. Yield: 16.4 g of intermediate compound 12.

Example A2 a. Preparation of Intermediate Compound 3

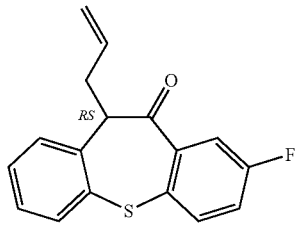

Reaction under $N_2$: a mixture of 2-fluoro-dibenzo[b,f]thiepin-1,1-(10H)-one (0.0347 mol) in dry THF (40 mL) was added dropwise to a suspension of NaH (60% in mineral oil) (0.0371 mol) in dry THF (80 mL). The reaction mixture was cooled on an ice-bath and then allowed to reach room temperature, then the mixture was stirred for 1 hour and a mixture of 3-bromo-1-propene (0.0347 mol) in dry THF (30 mL) was added dropwise. The reaction mixture was stirred at room temperature for 16 hours, then quenched with a saturated $NH_4Cl$ solution and extracted with $CH_2Cl_2$. The organic layer was dried ($Na_2SO_4$) and the solvent was evaporated. This residue was purified by short open column chromatography, the product fractions were collected and the solvent was evaporated. Yield: 7.57 g of intermediate compound 3 (77%).

b. Preparation of Intermediate Compound 4

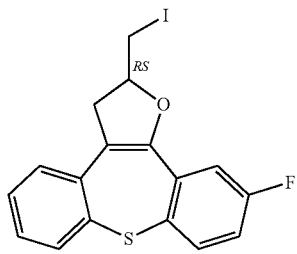

Reaction under $N_2$: bis(pyridine)iodine(I) tetrafluoroborate (0.0015 mol) was added to a solution of intermediate compound 3 (prepared according to A2.a) (0.00145 mol) in dry $CH_2Cl_2$ (50 mL) at room temperature, then the reaction mixture was quenched with aqueous sodium thiosulphate. The organic layer was separated, washed with brine and with water, dried ($Na_2SO_4$) and the solvent was evaporated (vacuum). The residue was purified by short open column chromatography. The product fractions were collected and the solvent was evaporated. Yield: 0.3 g of intermediate compound 4 (50%).

Example A3 a. Preparation of Intermediate Compound 5

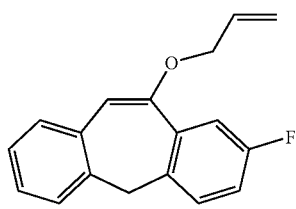

A mixture of 2-fluoro-5,10-dihydro-11H-dibenzo[a,d]cyclohepten-11-one (0.3027 mol), 3-bromo-1-propene (0.303 mol), $K_2CO_3$ (0.605 mol) in N,N-dimethylformamide (500 mL) was mixed and heated overnight at 60° C. Water and toluene were added and the organic layer was separated, then the aqueous layer was extracted 2 times with toluene. The organic layers were combined, washed 2 times with water and with brine, then dried ($Na_2SO_4$) and the solvent was evaporated (vacuum). The residue was purified by high-performance liquid chromatography; the product fractions were collected and the solvent was evaporated. Yield: 40 g of intermediate compound 5 (49.6%).

b. Preparation of Intermediate Compound 6

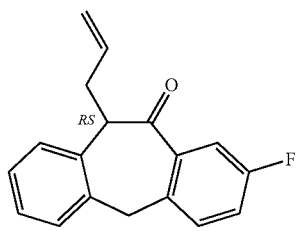

A solution of intermediate compound 5 (prepared according to A3.a) (0.150 mol) in toluene (200 mL) was heated at 220° C. (reaction temperature) for 10 hours in a high pressure Parr reactor vessel, then the reaction mixture was cooled to room temperature and the solvent was evaporated (vacuum). The residue was purified by short open column chromatography over silica gel (eluent: $CH_2Cl_2$). The product fractions an were collected and the solvent was evaporated. Yield: 20 g of intermediate compound 6 (50%).

c. Preparation of Intermediate Compound 7

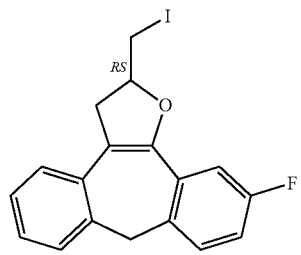

Reaction under $N_2$: bis(pyridine)iodine(I) tetrafluoroborate (0.0826 mol) was added to a solution of intermediate compound 6 (prepared according to A3.b) (0.07515 mol) in dry $CH_2Cl_2$ (q.s.) at room temperature and the reaction mixture was stirred for 0.5 h, then the reaction mixture was quenched with aqueous sodium thiosulphate. The organic layer was separated, washed with brine and with water, dried ($Na_2SO_4$) and the solvent was evaporated (vacuum). The residue was purified by short open column chromatography, then the product fractions were collected and the solvent was evaporated giving the intermediate compound 7 (92%).

d. Preparation of Intermediate Compound 18

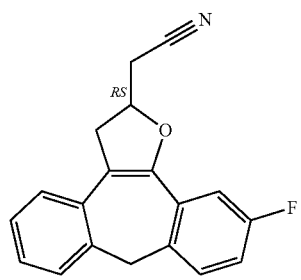

A mixture of intermediate compound 7 (prepared according to A3.c) (0.0051 mol) and KCN (0.0102 mol) in DMF (5 mL) and $H_2O$ (1 mL) was stirred for 4 hours at 60° C. in a sealed tube. The resultant mixture was diluted with water, then extracted with EtOAc. The organic layer was separated, dried, filtered and the solvent evaporated under reduced pressure. The residue was purified by short column chromatography over silica gel. The product fractions were collected and the solvent was evaporated. Yield: 0.98 g of intermediate compound 18 (66%).

Example A4 a. Preparation of Intermediate Compound 8

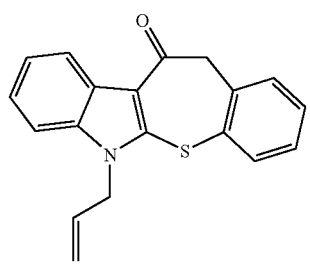

A mixture of NaH (60% in mineral oil) (0.00746 mol) in THF (q.s.) was stirred under $N_2$ at room temperature and a mixture of 6H-[1]benzothiepino[2,3-b]indol-11(12H)-one (0.00678 mol) in THF (q.s.) was added, then the resulting suspension was stirred for 3 hours and a mixture of 3-bromo-1-propene (0.00746 mol) in THF (q.s.) was added dropwise. The resulting solution became gradually a suspension and the reaction mixture was stirred for 16 hours, then a saturated $NH_4Cl$ solution was added. The organic layer was separated, washed with water and with brine, dried, filtered off and the solvent was evaporated. The residue was purified by short open column chromatography. The product fractions were collected and the solvent was evaporated. Yield: 1.8 g intermediate compound 8.

b. Preparation of Intermediate Compound 9

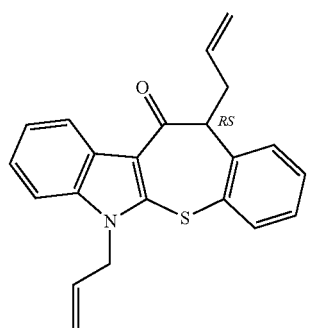

A mixture of NaH (60%) (0.0046 mol) in THF (q.s.) was stirred under $N_2$ and a mixture of intermediate compound 8 (0.00418 mol) in THF (q.s.) was added, then the resulting mixture was stirred for 4 hours at room temperature and a mixture of 3-bromo-1-propene (0.0046 mol) in THF (q.s.) was added dropwise. The reaction mixture was stirred for 16 hours and a satd. $NH_4Cl$ solution was added. The organic layer was separated, dried, filtered off and the solvent was evaporated. Yield: 0.848 g of intermediate compound 9 (used as such in the next reaction step without further purification).

c. Preparation of Intermediate Compound 10

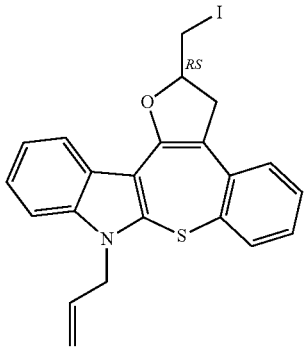

A mixture of intermediate compound 9 (0.00029 mol) in CH$_2$Cl$_2$ (15 mL) was stirred under N$_2$ at room temperature and bis(pyridine)iodine(I) tetrafluoroborate (0.00035 mol) was added, then the reaction mixture was stirred for 30 minutes and a saturated Na$_2$S$_2$O$_3$ solution was added. The organic layer was separated, dried and the solvent was evaporated. The residue was purified by short open column chromatography (eluent: EtOAc/Heptane 1/4). The product fractions were collected and the solvent was evaporated. Yield: 0.1 g of intermediate compound 10.

Example A5 a. Preparation of Intermediate Compound 13

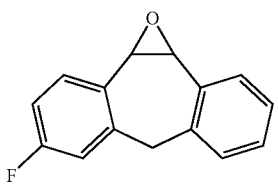

3-chlorobenzenecarboperoxoic acid (previously dried, 0.07 mol) in CH$_2$Cl$_2$ (q.s.) was added dropwise to a mixture of 2-fluoro-5H-dibenzo[a,d]cycloheptene (prepared according to the teachings in WO 03/040122 and WO 99/19317 of which the content is included herein) (0.046 mol), hydroquinone (catalytic quantity) and NaHCO$_3$ (0.093 mol) in CH$_2$Cl$_2$ (q.s.), stirred an refluxed. The reaction mixture was stirred and refluxed for 3 hours, then cooled and washed three times with a saturated NaHCO$_3$ solution. The organic layer was separated, dried (Na$_2$SO$_4$), filtered and the solvent was evaporated. Yield: 10.05 g of intermediate compound 13.

b. Preparation of Intermediate Compound 14

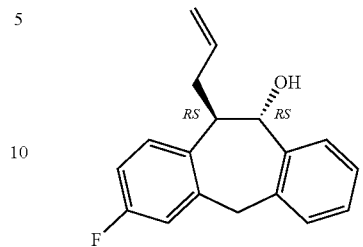

A solution of intermediate compound 13 (prepared according to A5.a) (0.044 mol) in THF (100 mL) was cooled on an ice-water bath under N$_2$ and then bromo-2-propenyl magnesium (0.05745 mol; 1.0 M) was added dropwise. The reaction mixture was stirred and refluxed for 2 hours. The mixture was cooled, then carefully treated with a NH$_4$Cl solution and extracted with EtOAc. The organic layer was separated, dried (Na$_2$SO$_4$), filtered off and the solvent was evaporated. The dry residue was purified by short open column chromatography (eluent: Heptane/EtOAc 85/15). The product fractions were collected and the solvent was evaporated. Yield: 6 g of intermediate compound 14 (51%).

c. Preparation of Intermediate Compounds 15 and 16

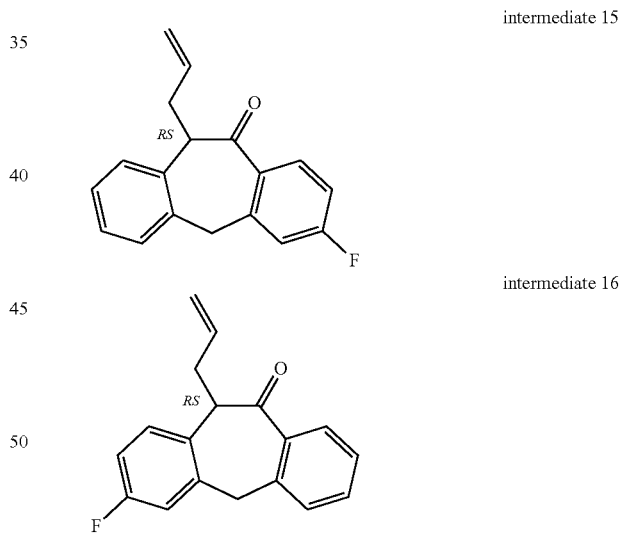

A mixture of intermediate compound 14 (prepared according to A5.b) (0.00473 mol), Pyridinium chlorochromate (0.0071 mol) and NaOAc (0.0123 mol) in CH$_2$Cl$_2$ (100 mL) was stirred for 2 hours at room temperature, then the reaction mixture was diluted with CH$_2$Cl$_2$ (100 mL) and filtered over silica gel. The organic layer was concentrated and the solvent was evaporated under reduced pressure. The obtained residue (1 g) was purified by short open column chromatography (eluent: Heptane/EtOAc 95/5). Two product fractions were collected and the solvent was evaporated. Yield fraction 1:0.21 g of intermediate compound 15 and yield fraction 2:0.3 g of intermediate compound 16.

d. Preparation of Intermediate Compound 17

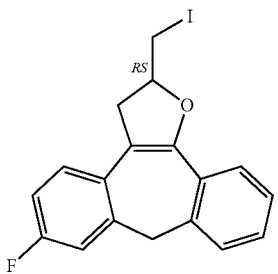

A mixture of intermediate compound 16 (prepared according to A5.c) (0.0011265 mol) and bis(pyridine)iodine(I) tetrafluoroborate (0.0013518 mol) in CH$_2$Cl$_2$ (50 mL) was stirred under N$_2$ for 1 hour at room temperature and then the reaction mixture was washed with Na$_2$S$_2$O$_3$, with 1N HCl, with H$_2$O and with brine. The organic layer was separated, dried (Na$_2$SO$_4$), filtered off and the solvent was evaporated. The residual oil was purified by short open column chromatography (eluent: Heptane/EtOAc 9/1). The product fractions were collected and the solvent was evaporated. Yield: 0.330 g of intermediate compound 17 (75%).

Example A6 a. Preparation of Intermediate Compounds 27, 28

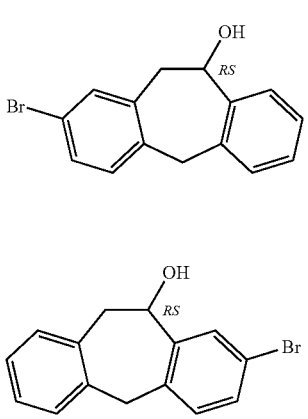

A mixture of 2-bromo-5H-Dibenzo[a,d]cycloheptene (5.38 g; 0.02 mol) in THF (250 mL) at r.t., NaBH$_4$ (3 g; 0.079 mol) was added portionwise. A solution of boron trifluorate etherate (12.93 mL, 0.105 mol) in THF (40 mL) was added dropwise. The resulting mixture was stirred at rt for 24 h. Water (30 mL) and methanol (30 mL) were carefully added. NaOH (3 M; 100 mL) was added followed of 15 mL of H$_2$O$_2$ (30% v/v). The resulting mixture was stirred at room temperature for 4 hours. Et$_2$O (150 mL) and EtOAc (100 mL) were added. Layers were separated and the organic one was washed with brine and water, dried (Na$_2$SO$_4$) and vacuum concentrated, affording a mixture of intermediate compounds 27 and 28 b. Preparation of Intermediate Compounds 29, 30

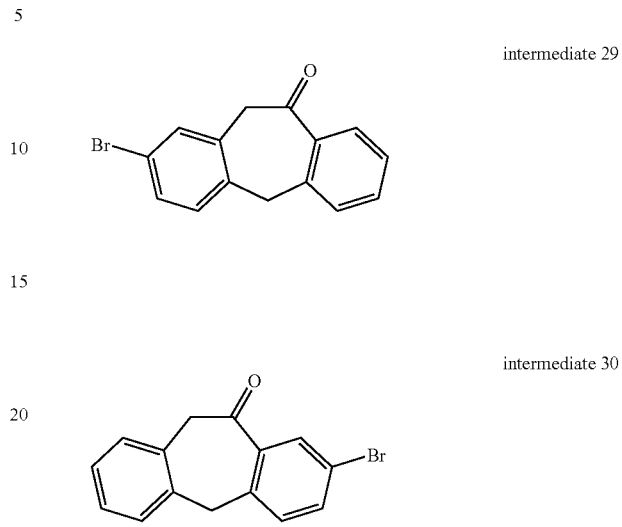

To a mixture of intermediate compounds 27 and 28 (2 g; 6.92 mmol) in CH$_2$Cl$_2$ (40 mL), pyridinium chlorocbromate (2.84 g; 13.14 mmol) was added and the resulting mixture was stirred for 3 hours. The mixture was filtered over silicagel and the filtrate was vacuum concentrate. The residue thus obtained was purified by flash chromatography (eluent: heptane/CH$_2$Cl$_2$, 4:1) to give intermediate compound 29 and intermediate compound 30.

c. Preparation of Intermediate Compound 21

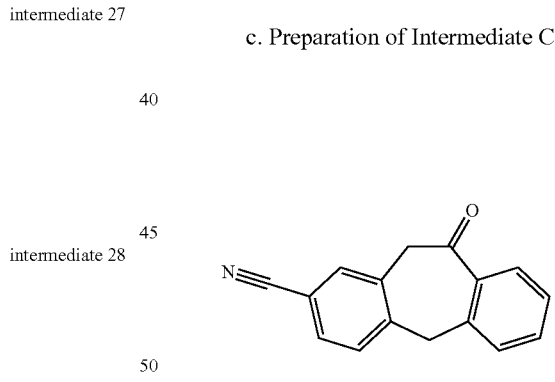

A mixture of intermediate compound 29 (0.0021 mol), Zn(CN)$_2$ (0.00136 mol) and Pd(PPh$_3$)$_4$ (0.00021 mol) in DMF (5 ml; previously deoxygenated) was stirred at room temperature and the reaction mixture was heated under microwave conditions for 15 minutes at 120° C. The mixture was filtered and the solvent (DMF) was evaporated. The obtained residue was diluted with EtOAc and then washed with H$_2$O and with brine. The organic layer was separated, dried (Na$_2$SO$_4$), filtered off and the solvent was evaporated. The residual oil was purified by column chromatography over silica gel (eluent: Heptane/EtOAc 85/15). The product fractions were collected and the solvent was evaporated. Yield: 0.350 g of intermediate compound 21 (58%).

d. Preparation of Intermediate Compound 22

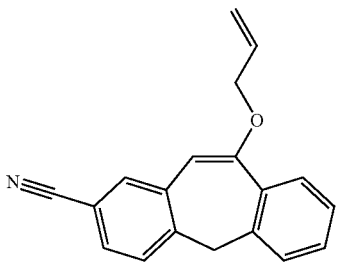

A mixture of intermediate compound 21 (prepared according to A6.c) (0.0015 mol), 3-bromo-1-propene (0.00165 mol) and K$_2$CO$_3$ (0.003 mol) in DMF (15 mL) was stirred for 16 hours at 60° C. and then H$_2$O and EtOAc were added. The organic layer was separated and the aqueous layer was extracted 2 times with EtOAc. The organic layers were combined, washed 2 times with brine and with water, then dried (Na$_2$SO$_4$), filtered and the solvent was evaporated. Yield: 0.330 g of intermediate compound 22 (80%).

e. Preparation of Intermediate Compound 23

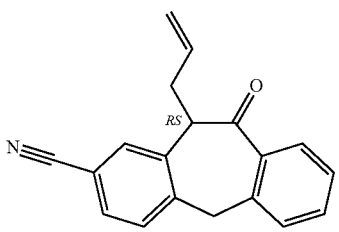

A mixture of intermediate compound 22 (prepared according to A6.d) (0.001 mol) in toluene (25 mL) was stirred for 16 hours at 190° C. and then the solvent was evaporated. Yield: 0.1 g of intermediate compound 23 (33%).

f. Preparation of Intermediate Compound 23

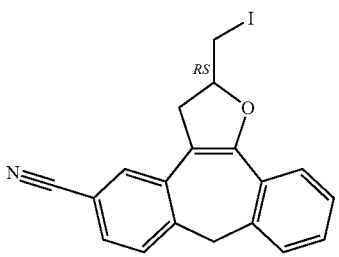

A mixture of intermediate compound 23 (prepared according to A6.e) (0.000366 mol) and bisyridine) iodine (1$^+$), tetrafluorate (1$^-$) (0.000439 mol) in CH$_2$Cl$_2$ (20 ml) was stirred for 1 hour at room temperature and under N$_2$, then the reaction mixture was washed with Na$_2$S$_2$O$_3$, with H$_2$O and with brine. The organic layer was separated, dried (Na$_2$SO$_4$), filtered off and the solvent was evaporated. The residual oil was purified by short open column chromatography over silica gel (eluent: Heptane/EtOAc 9/1). The product fractions were collected and the solvent was evaporated. Yield: 0.04 g of intermediate compound 24 (27%).

This intermediate compound 24 is used as starting material for final compound 133 which is prepared according to B2.b.

Example A7 a. Preparation of Intermediate Compound 25

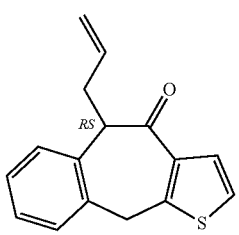

A mixture of NaH (60%) (0.059 mol) in THF (q.s.) was stirred at −30° C. under N$_2$ and a mixture of 5,10-dihydro-4H-benzo[5,6]cyclohepta[1,2-b]thiophen-4-one (0.056 mol) in THF (q.s.) was added dropwise in 30 minutes, then the resulting mixture was gradually warmed to room temperature and stirred for 1 hour. A mixture of 3-bromo-1-propene (0.056 mol) in THF (50 mL) was added dropwise in 30 minutes and the reaction mixture was stirred for 16 hours. A 10% NH$_4$Cl solution was added and the mixture was stirred for 15 minutes, water was added and the aqueous solution was extracted with CH$_2$Cl$_2$. The organic layer was separated, dried (Na$_2$SO$_4$), filtered off and the solvent was evaporated under reduced pressure. The residue was purified by short open column chromatography (eluent: CH$_2$Cl$_2$). The product fractions were collected and the solvent was evaporated. Yield: 9.82 g of intermediate compound 25 (68%).

b. Preparation of Intermediate Compound 26

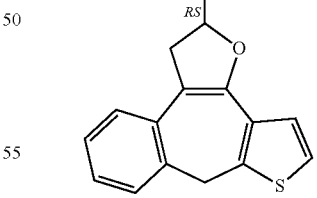

I$_2$ (0.005 mol) was added to a solution of intermediate compound 25 (prepared according to A7.a) (0.001 mol) in THF (4 mL) and the resultant reaction mixture was stirred overnight at room temperature. A saturated aqueous Na$_2$S$_2$O$_3$ solution (2 mL) was added and the mixture was stirred vigorously. Then, the mixture was extracted with EtOAc (3×5 mL). The organic layer was separated, dried (MgSO$_4$), filtered and the solvent was evaporated. The residue was purified by column chromatography over silica gel (eluent:

EtOAc/heptane 5/95). The product fractions were collected and the solvent was evaporated. Yield: 0.083 g of intermediate compound 26 (39%).

c. Preparation of Intermediate Compound 31

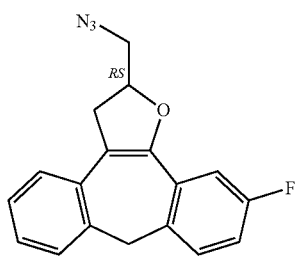

A mixture of intermediate compound

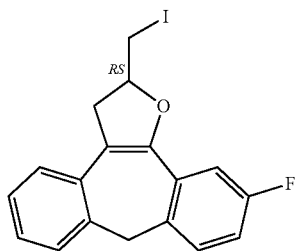

(1.6 g; 4.08 mmol, prepared according to A5.d) NaN₃ (0.56 g; 8.57 mmol) in DMF (20 mL) was heated at 85° C. (oil bath temperature) for 16 hours. The solvent was evaporated in vacuo and the resulting residue was taken up in CH₂Cl₂ and washed with water and brine, dried (Na₂SO₄), filtered and vacuum concentrated to give 1.13 g of intermediate compound 31. (Yield: 90%)

B. Preparation of the Final Compounds

The compounds prepared hereinunder all are mixtures of isomeric forms, unless otherwise specified.

Example B1 a) Preparation of Final Compound 3

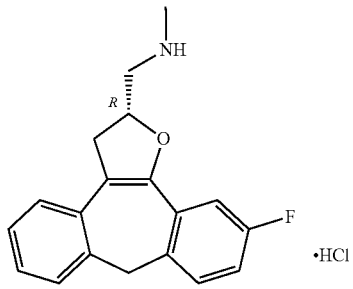

A solution of intermediate compound 2 (prepared according to A1.b1) (290 g; 0.664 mol) and N-methylamine, 40% aqueous solution (1.2 L) in 700 mL toluene was stirred during 16 hours at 90° C. in a high-pressure Parr apparatus. Subsequently, the layers were separated and 1 L of toluene was added to the organic layer. After washing the organic layer three times with water (3×1.5 L), 1.5 L of 10% $CH_3COOH/H_2O$ was added and the layers were separated. The water layer was neutralized to pH=10 with a saturated aqueous $K_2CO_3$ solution and extracted with 2 L of toluene. The toluene layer was dried over $MgSO_4$, filtered and concentrated under vacuum. Subsequently, the residue was refluxed in 1.1 L of MTBE and 85 mL of HCl/iPrOH 6N was added over 30 minutes, after which the solution was refluxed for an additional hour. The precipitate was filtered off and dried under reduced pressure at 45° C. Yield: 132 g of final compound 3 (60%).

b) Preparation of Final Compound 139

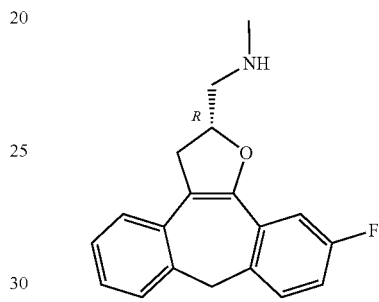

A mixture of intermediate compound 2 (prepared according to A1.b1) (0.0023 mol) and CaO (q.s.) in $CH_3NH_2$ (40 mL; 2.0 M) and THF (30 mL) was stirred for 16 hours in a high-pressure Parr reactor vessel at 120° C., then the resulting suspension was filtered over celite and the filtrate was evaporated under reduced pressure. The obtained residue was dissolved in $CH_2Cl_2$ and the solution was washed with $NaHCO_3$, with brine and water, then dried ($Na_2SO_4$), filtered off and the solvent was evaporated. The residual oil was purified by short open column chromatography (eluent: $CH_2Cl_2/(CH_3OH/NH_3)$ 97/3). The product fractions were collected and the solvent was evaporated. Yield: 0.46 g of final compound 139 (68%).

c) Preparation of Final Compound 103

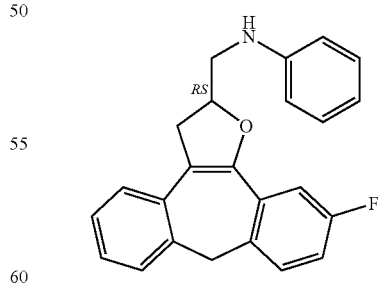

A mixture of intermediate compound 12 (prepared according to A1.b1 (0.000343 mol), phenylamine (0.00103 mol) and KI (0.000343 mol) in $CH_3CN$ (2 mL) was stirred for 45 minutes at 195° C. in a microwave oven. The reaction mixture was diluted with $CH_2Cl_2$ (40 mL), then washed several times with water and brine. The organic layer was separated, dried ($Na_2SO_4$), filtered and the solvent was evaporated. The residue (oil) was purified by short open column chromatography over silica gel (eluent: $CH_2Cl_2$/heptane 1/1). The product fractions were collected and the solvent was evaporated to give final compound 103.

Example B2 a. Preparation of Final Compound 18

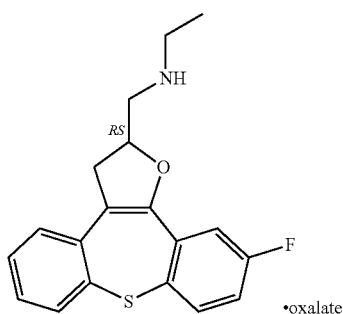

•oxalate

A mixture of intermediate compound 4 (prepared according to A2.b) (0.00085 mol), ethylamine (0.0085 mol) and CaO (0.0085 mol) in THF (q.s.) was heated at 140° C. for 16 hours, then the suspension was filtered through celite and the filtrate was evaporated. The residue was dissolved in $CH_2Cl_2$, washed with a 10% $NaHCO_3$ solution and dried ($Na_2SO_4$). The solvent was evaporated and the residue was purified by short open column chromatography (eluent: $CH_2Cl_2$/($CH_3OH/NH_3$ saturated) 97/3. The product fractions were collected and the solvent was evaporated. The oily residue was converted into the ethanedioic acid salt and the desired product was collected by filtration and dried in vacuo. Yield: 0.140 g of final compound 18 (m.p.: 240.7° C.).

b. Preparation of Final Compound 134

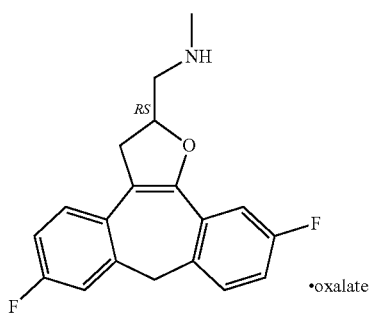

•oxalate

A mixture of intermediate compound 17 (prepared according to A5.d) (0.00084 mol) and CaO (1 g) in $CH_3NH_2$ (15 mL; 2.0M in THF) and THF (15 mL) was stirred in a high-pressure Parr reactor vessel for 16 hours at 120° C. The reaction mixture was filtered over celite and the filtrate was evaporated under reduced pressure. The residue was dissolved in $CH_2Cl_2$ (100 mL), then this solution was washed with $NaHCO_3$ (3×50 mL), with water (3×50 mL) and with brine (2×50 mL). The organic layer was separated, dried ($Na_2SO_4$), filtered off and the solvent was evaporated. The residual oil was purified by short open column chromatography (eluent: $CH_2Cl_2$/($CH_3OH/NH_3$) 95/5). The product fractions were collected and the solvent was evaporated. The residue was converted into the ethanedioic acid salt and then the resulting solid was collected and dried in vacuo.

Yield: 0.170 g of final compound 134 (68%).

c. Preparation of Final Compound 100 and 27 (Oxalate Salt)

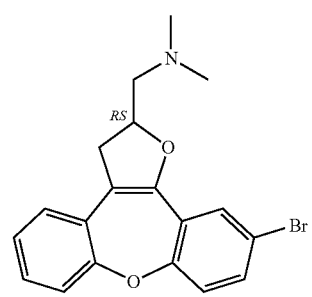

final compound 100

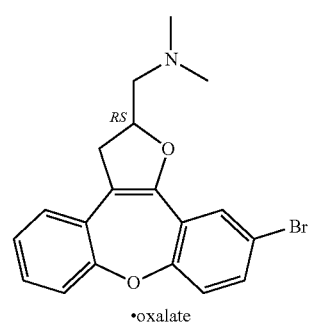

final compound 27

•oxalate

A mixture of

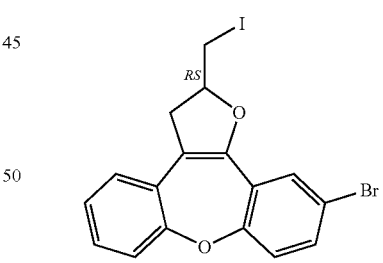

(prepared according to A2.b) (0.00176 mol) and CaO (0.300 g) in N,N-dimethylamine (10 mL, 2 M in THF) and THF (15 mL) was mixed and heated at 130° C. (oil bath temperature) for 8 hours in a Parr reactor vessel, then the reaction mixture was cooled to room temperature and the solids were filtered off. The solvent was evaporated and the residue was purified by short open column chromatography. The product fractions were collected and the solvent was evaporated. Yield: 0.605 g (92.5%) of final compound 100. A part of the residue was treated with oxalic acid in $EtO_2$ and converted into the ethanedioic acid salt. The resulting precipitate was collected and dried in vacuo. Yield: 57.2 mg of final compound 27.

Example B3

Preparation of Final Compounds 93 and 94 final compound 93

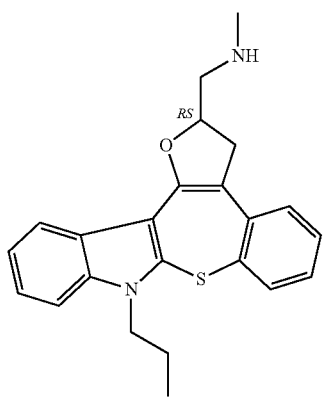

final compound 94

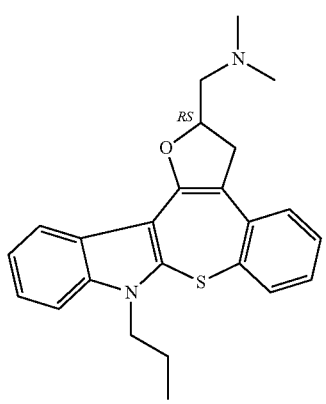

A mixture of

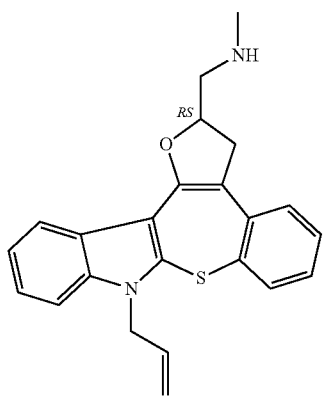

(prepared according to A4.c) (0.00019 mol) in methanol (15 mL) was hydrogenated with Pd/C (0.050 g) as a catalyst. After uptake of $H_2$ (1 equivalent), the catalyst was filtered off and the filtrate was evaporated and then evaporated under reduced pressure. The residue was purified by short open column chromatography over silica gel (eluent: $CH_2Cl_2$/$CH_3OH$ 98/2). Two product fractions were collected and the solvent was evaporated. Yield Fraction 1:0.017 g of final compound 93. Yield Fraction 2:0.0143 g of final compound 94.

Example B4

Preparation of Final Compound 31

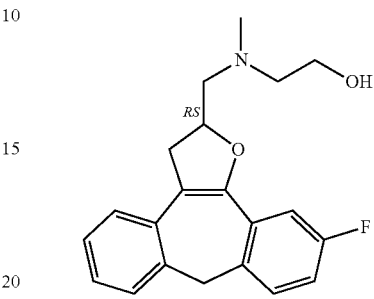

Procedure for compound 31, 33, 35, 36, 37, 38, 39, 40, 41 and 43: (reaction performed in a microwave oven). A mixture of intermediate compound 7 (prepared according to A3.c) (0.00043 mol) and 2-(methylamino)ethanol (0.00172 mol) in $CH_3CN$ (10 mL) was mixed and heated at 130° C. under microwave conditions (from room temperature to 130° C. in 5 min., P (max.): 600 W) for 20 minutes. The solvent $CH_3CN$ was evaporated and the resulting concentrate was taken up in $CH_2Cl_2$, then, washed with a saturated aqueous $NaHCO_3$ solution. The organic layer was separated, dried ($Na_2SO_4$) and the solvent was evaporated (vacuum). The residue was taken up in $CH_2Cl_2$ (4 mL) and PS-isocyanate (nucleophile scavenger) (0.00344 mol) was added. The resulting mixture was shaken overnight in a Bohdan apparatus and the resin was filtered off. PS-TsOH (polymer bound acid) (0.00344 mol) was added to the solution and the mixture was shaken for 3 hours. The solvent was removed by filtration and $CH_3OH$ was added to the residue. The resulting mixture was shaken for 30 minutes and the solvent was filtered off again. Liquids were discarded. A saturated $CH_3OH$/$NH_3$ solution was added to the residue and the mixture was shaken for 1 hour, then the resin was filtered off and the solvent was evaporated. The residue thus obtained was treated with oxalic acid in $EtO_2$ and converted into the ethanedioic acid salt. The resulting precipitate was collected and dried under vacuo yielding final compound 31.

Example B5 a. Preparation of Final Compound 22

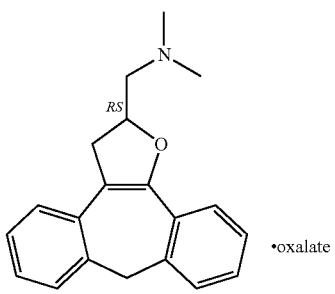

•oxalate

A mixture of final compound 21 (prepared according to B2.a except for the last step where the compound was converted into its salt) (0.00243 mol) in methanol (30 mL) was hydrogenated for 12 hours at 60 psi with Pd/C 10% (cat. quant.) as a catalyst. After uptake of 12 (1 equivalent), the catalyst was filtered off and the filtrate was evaporated. The residue was crystallised from $Et_2O/CH_2Cl_2$ and then the resulting precipitate was collected. Yield: 0.450 g of final compound 22 (m.p.: 172.8° C.).

b. Preparation of Final Compounds 101 and 25

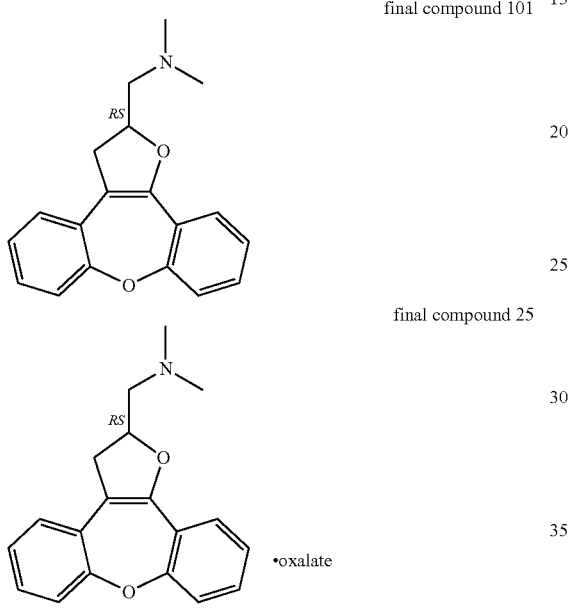

final compound 101 final compound 25

•oxalate

Reaction under $N_2$: a solution of final compound 100 (prepared according to B2.b) (0.00158 mol) in THF, dry (25 mL) was cooled to −78° C. and then n-BuLi, 1.6 M in Hexane (0.0016 mol) was added dropwise. The reaction mixture was allowed to slowly reach room temperature, water was added and the organic solvent (IF) was evaporated. The aqueous concentrate was extracted 2 times with $CH_2Cl_2$ and the organic layers were combined, then dried ($Na_2SO_4$). The solvent was evaporated (vacuum) and the residue was purified by short open column chromatography over silica gel (eluent: $CH_2Cl_2/(CH_3OH/N_3)$ 100/0, 98/2). The product fractions were collected and the solvent was evaporated. Yield: 70 mg of final compound 101. The residue was treated with oxalic acid in $EtO_2$ and converted into the ethanedioic acid salt. The resulting precipitate was collected and dried. Yield: 69 mg of final compound 25.

Intermediate compound 7 (prepared according to A3.c) (1 equivalent) was dissolved in $CH_2Cl_2$ (q.s) and butylisocyanate (1 equivalent) was added at once. The vials were shaken overnight in a Bohdan apparatus. PS-triamine (3 equivalents, electrophile scavenger) and PS-isocyanate (3 equivalents, (nucleophile scavenger) were added to the vials, to scavenge the reactants, and the reaction mixtures was shaken for 6 hours. The resins were filtered off and washed twice with $CH_2Cl_2$. The combined organic layers were shaken with Amberlyst 15 (3 equivalents) in a Bohdan apparatus overnight (first step of a catch and release process). The resin was filtered off and washed twice with MeOH. The liquids were discarded. The resin was shaken twice with MeOH($NH_3$) for 3 hours and filtered off (second step of a catch and release process). The combined methanolic phases were evaporated. This residue was taken up in $CH_2Cl_2$ and trifluoroacetic acid (2 equivalents) was added; after stirring for 2 hours at room temperature volatiles were evaporated and the residue was dried, affording the final compound 77.

Example B6 a. Preparation of Final Compound 51

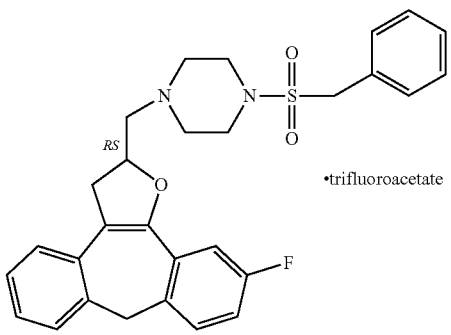

•trifluoroacetate

Reaction procedure for compounds 44, 46, 48, 49 and 51.

Intermediate compound 7 (prepared according to A3.c) (1 equivalent) was dissolved in $CH_2Cl_2$ (q.s.) and PS-DIEA (polymer bound base) (3 equivalents) was added at room temperature. Benzenemethanesulfonyl chloride (1 equivalent) was added at once. The vial was shaken overnight in a Bohdan apparatus. PS-trisamine (3 equivalents, electrophile scavenger) and PS-isocyanate (3 equivalents, nucleophile scavenger) were added to the vial and the reaction mixture was shaken for 6 hours. The resins were filtered off and washed twice with $CH_2Cl_2$. The combined organic layers were shaken with Amberlyst 15 (3 equivalents) in a Bohdan apparatus overnight (first step of a catch and release process). The resin was filtered off and washed twice with $CH_3OH$ ($NH_3$) for 3 hours and filtered off (second step of a catch and release process). The combined methanolic phases were evaporated and the residue thus obtained was analysed by LCMS (if the compound is not pure enough, it is purified by HPLC before the treatment with trifluoroacetic acid). This residue was taken up in $CH_2Cl_2$ and trifluoroacetic acid (2 equivalents) was added; after stirring for 2 hours at room temperature volatiles were evaporated and the residue was dried, affording the final compound 51. Yield (Model Reaction): 0.137 g of final compound 51.

b. Preparation of Final Compound 77

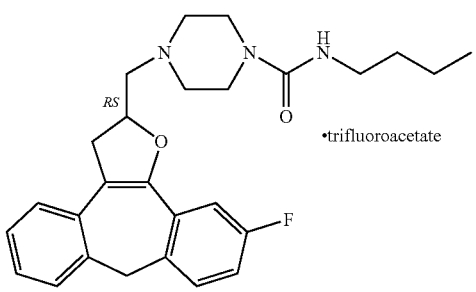

•trifluoroacetate

Reaction procedure for compounds 77, 79, 81, 83, 85, 87 and 89.

Intermediate compound 7 (prepared according to A3.c) (1 equivalent) was dissolved in CH$_2$Cl$_2$ (q.s.) and butylisocyanate (1 equivalent) was added at once. The vials were shaken overnight in a Bohdan apparatus. PS-trisamine (3 equivalents, electrophile scavenger) and PS-isocyanate (3 equivalents, nucleophile scavenger) were added to the vials, to scavenge the reactants, and the reaction mixtures was shaken for 6 hours. The resins were filtered off and washed twice with CH$_2$Cl$_2$. The combined organic layers were shaken with Amberlyst 15 (3 equivalents) in a Bohdan apparatus overnight (first step of a catch and release process). The resin was filtered off and washed twice with CH$_3$OH. The liquids were discarded. The resin was shaken twice with CH$_3$OH(NH$_3$) for 3 hours and filtered off (second step of a catch and release process). The combined methanolic phases were evaporated. This residue was taken up in CH$_2$Cl$_2$ and trifluoroacetic acid (2 equivalents) was added; after stirring for 2 hours at room temperature volatiles were evaporated and the residue was dried, affording the final compound 77.

Example B7 a. Preparation of Final Compound 140

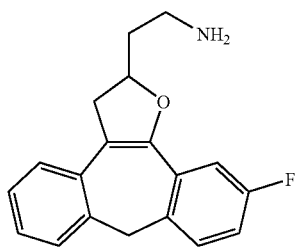

A mixture of intermediate compound 18 (prepared according to A3.d) (0.00336 mol) in saturated NH$_3$/CH$_3$OH (q.s.) was hydrogenated for 2 hours at room temperature under 40 psi of pressure with Raney Nickel as a catalyst. After uptake of H$_2$ (2 equivalents), the catalyst was filtered off and the filtrate was evaporated under reduced pressure. The residue was taken up into CH$_2$Cl$_2$, washed with a saturated aqueous NaHCO$_3$ solution, dried (Na$_2$SO$_4$), filtered and the solvent evaporated. The residue was purified by short open column chromatography over silica gel (eluent: CH$_2$Cl$_2$/(CH$_3$OH/NH$_3$) 96/4). The product fractions were collected and the solvent was evaporated. Yield: 0.760 g of final compound 140.

b. Preparation of Final Compounds 137 and 141

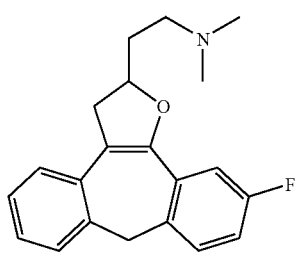

compound 137
•hydrochloride salt

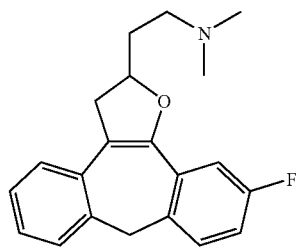

compound 141

A mixture of final compound 140 (prepared according to B7.a) (0.000339 mol), HCHO, 37 wt % in water (0.00135 mol) and formic acid (0.00271 mol) in CH$_3$OH (5 mL) was stiffed and re-fluxed for 6 hours. The solvent was evaporated under reduced pressure. The residue was redissolved in CH$_2$Cl$_2$. The organic solution was washed with a saturated aqueous NaHCO$_3$ solution, dried (Na$_2$SO$_4$), filtered and the solvent evaporated under reduced pressure. The residue was purified by short open column chromatography over silica gel (eluent: CH$_2$Cl$_2$/(CH$_3$OH/NH$_3$) 97/3). The product fractions were collected and the solvent was evaporated. Yield: 0.0815 g of final compound 141 (74.4%). Final compound 141 was converted into the hydrochloric acid salt (1:1), filtered off and dried. Yield: 0.080 g of final compound 137.

Example B8 a. Preparation of Final Compound 142

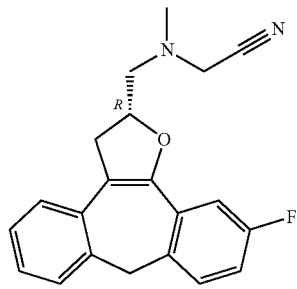

A mixture of final compound 139 (prepared according to B1.b) (0.01439 mol), chloroacetonitrile (0.01439 mol) and K$_2$CO$_3$ (0.036 mol) ub DMF (q.s.) was stirred for 16 hours at 100° C. The reaction mixture was diluted with EtOAc, then washed with water, dried (Na$_2$SO$_4$), filtered and the solvent evaporated affording final compound 142.

b. Preparation of Final Compound 125

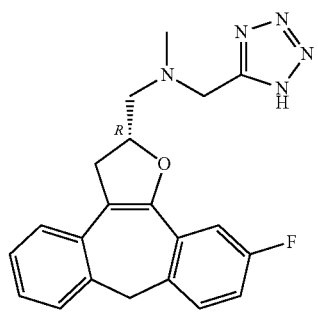

A mixture of final compound 142 (prepared according to B8.a) (0.00060 mol), azidotrimethyl silane (0.00180 mol) and dibutyloxystannane (0.00012 mol) in toluene (3 mL) was heated for 5 minutes at 170° C. The solvent was evaporated. The residue was purified by short open column chromatography (eluent: CH$_2$Cl$_2$/CH$_3$OH 96/4; then 80/20). The product fractions were collected and the solvent was evaporated. The residue was washed with diethyl ether, then dried. Yield: 0.108 g of final compound 125 (48%).

c. Preparation of Final Compound 138

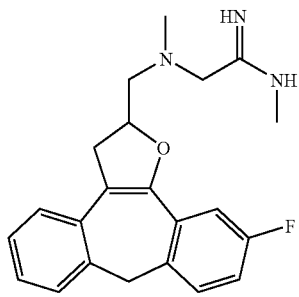

Reaction under N$_2$ atmosphere. Al(CH$_3$)$_3$, 2 M/hexane (0.0015 mol) was added dropwise to a mixture of methylamine (0.0015 mol) in toluene, dry (1 mL), stirred at 0° C. The reaction mixture was stirred for 2 hours at room temperature. A solution of final compound 142 (prepared according to B8.a) (0.00075 mol) in toluene, dry (1.5 mL) was added. The reaction mixture was heated in the microwave oven for 5 minutes at 150° C. Methanol (1 mL) was added. The mixture was treated with an aqueous NaHCO$_3$ solution and CH$_2$Cl$_2$. The organic layer was separated, dried (Na$_2$SO$_4$), filtered and the solvent was evaporated. The residue was purified by short open column chromatography (eluent: CH$_2$Cl$_2$/CH$_3$OH 4/1), then by HPLC. The product fractions were collected and the solvent was evaporated. Yield: 0.017 g of final compound 138.

Example B9 a. Preparation of Final Compound 143 and 113

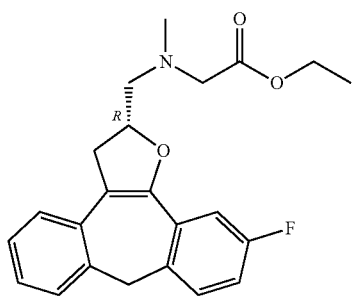

final compound 143

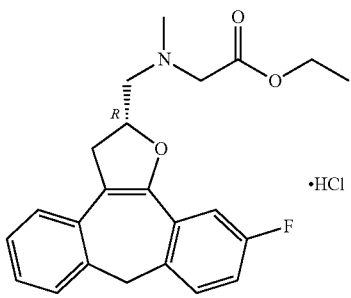

final compound 113

A mixture of final compound 139 (prepared according to B1.b) (0.021 mol), bromoacetic acid ethyl ester (0.021 mol) and K$_2$CO$_3$ (0.053 mol) in DMF (30 mL) was stirred and heated in a sealed tube for 16 hours at 100° C. The reaction mixture was cooled, diluted with EtOAc, washed with water (2×), dried, filtered and the solvent evaporated under reduced pressure. The residue was purified by short open column chromatography over silica gel (eluent gradient: CH$_2$Cl$_2$/(CH$_3$OH/NH$_3$) 100/0 to 99/1). The product fractions were collected and the solvent was evaporated. Yield: 7.65 g of final compound 143. An aliquot of final compound 143 was converted into the hydrochloric acid salt (1:1). The precipitate was filtered off and dried in vacuo to give final compound 113.

b. Preparation of Final Compound 107

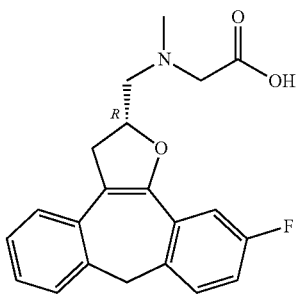

A solution of final compound 143 (prepared according to B9.a) (0.0181 mol) in THF (40 mL) was stirred at room temperature. A solution of LiOH (0.0199 mol) in H$_2$O (20 mL) was added dropwise and the resultant reaction mixture was stirred for 16 hours at room temperature. The mixture was acidified carefully with 2 N HCl until pH reached value 7. The resultant mixture was extracted with CH$_2$Cl$_2$, washed with brine, dried (Na$_2$SO$_4$), filtered and the solvent evaporated under reduced pressure. The residue was treated with diethyl ether, then dried. Yield: 4.58 g of final compound 107 (mp: 194.7° C.).

c. Preparation of Final Compound 120

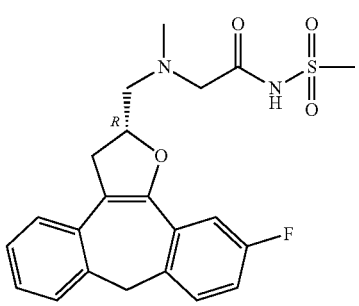

A mixture of final compound 107 (prepared according to B9.b) (0.00042 mol), HATU, (0.00051 mol) and Et$_3$N (0.00102 mol) in CH$_2$Cl$_2$ (5 mL) was stirred at room temperature. Methanesulfonamide (0.00127 mol) was added and the resultant reaction mixture was stirred for 16 hours at room temperature. The reaction mixture was washed with a saturated aqueous NaHCO$_3$ solution, dried (Na$_2$SO$_4$), filtered and the solvent was evaporated. The residue was purified by preparative HPLC. The product fractions were collected and the solvent was evaporated. Yield: 0.0982 g of final compound 120 (mp: 88.5° C.).

d. Preparation of Final Compound 123

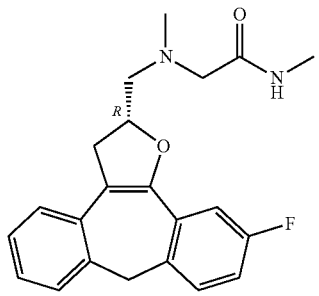

A mixture of final compound 108 (prepared according to B9.b) (0.000527 mol), HATU (0.000527 mol) and Et$_3$N (0.0012648 mol) in CH$_2$Cl$_2$ (q.s.) was stirred for 10 minutes at room temperature. CH$_3$NH$_2$, 2.0 M/THF (0.0015 mol) was added and the reaction mixture was stirred for 3 hours at room temperature. A saturated aqueous NH$_4$Cl solution was added. The organic layer was separated, washed with water and brine, dried (Na$_2$SO$_4$), filtered and the solvent was evaporated. The residue was purified by short open column chromatography over silica gel (eluent: CH$_2$Cl$_2$/(CH$_3$OH/NH$_3$) 97/3). The product fractions were collected and the solvent was evaporated. Yield: 0.020 g of final compound 123.

Example B10

Preparation of Final Compound 124

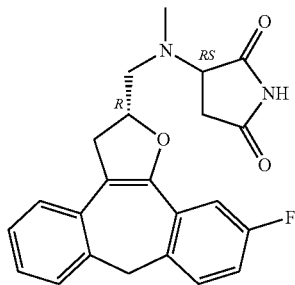

A mixture of final compound 139 (prepared according to B1.b) (0.001 mol) and 1H-pyrrole-2,5-dione (0.00092 mol) in EtOAc (3 mL) was stirred for 2 days at room temperature. The solvent was evaporated. The residue was purified by short open column chromatography over silica gel. The product fractions were collected and the solvent was evaporated. Yield: 0.292 g of final compound 124.

Example B11 a. Preparation of Final Compounds 144 and 2

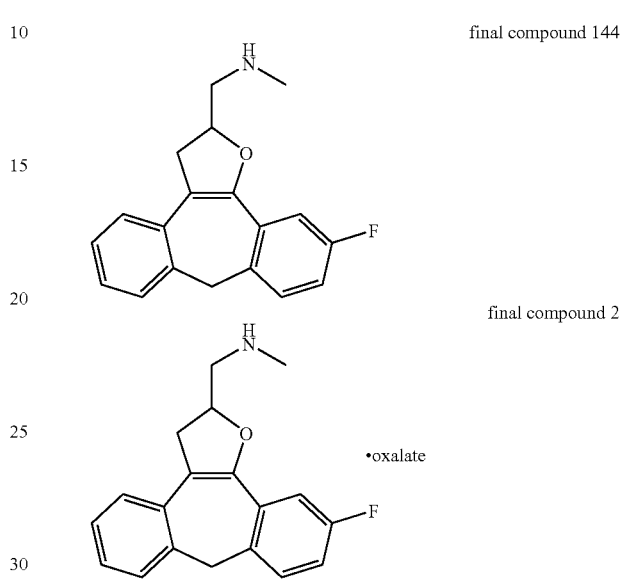

A mixture of intermediate compound 7 (prepared according to A3.c) (0.00058 mol), CH$_3$NH$_2$ (0.00586 mol) and CaO (0.100 g) in THF (20 mL) was stirred and heated at 130° C. (oil bath temperature) for 10 hours in a high-pressure Parr reactor vessel, then the reaction mixture was cooled to room temperature and the solids were filtered off. The organic solvent (THF) was evaporated, then the aqueous concentrate was taken up in CH$_2$Cl$_2$ and the mixture was washed with a saturated aqueous NaHCO$_3$ solution. The organic layer was separated, dried (Na$_2$SO$_4$) and the solvent was evaporated. The residue was purified in a manifold (vacuum) using Sep-Pak silica cartridge. The product fractions were collected and the solvent was evaporated to give final compound 144. Final compound 144 was treated with oxalic acid in EtO$_2$ and converted into the ethanedioic acid salt. The resulting precipitate was collected and dried in vacuo to give final compound 2.

b. Preparation of Final Compound 127

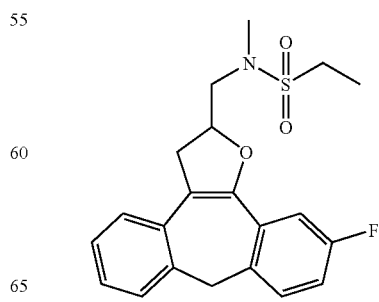

A mixture of final compound 144 (prepared according to B11.a) (0.003 mol), ethylsulfonylchloride (0.0033 mol) and Et₃N (0.0039 mol) in CH₂Cl₂ (50 mL) was stirred for 2 hours at room temperature. The resultant reaction mixture was washed with a 10% aqueous NaHCO₃ solution, with water, dried (Na₂SO₄), filtered and the solvent evaporated under reduced pressure. The residue was purified by short open column chromatography over silica gel (eluent: CH₂Cl₂/hexane 4/1). The product fractions were collected and the solvent was evaporated. Yield: 0.431 g of final compound 127.

Example B12

Preparation of Final Compounds 102

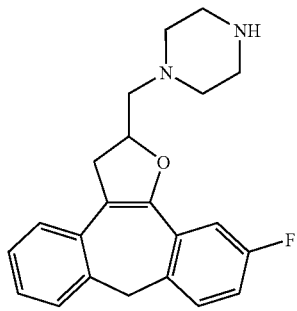

A mixture of intermediate compound 7 (prepared according to A3.c) (0.019 mol), piperazine (0.193 mol) and CaO (8.0 g) in THF (50 mL) was heated for 16 hours at 120° C. (oil batch temperature) in a high-pressure Parr reaction vessel and the resulting suspension was filtered over celite. The filtrate was evaporated under reduced pressure and the residue was partitioned between CH₂Cl₂/H₂O. After extraction of the aqueous layer, the organic layer was washed with NaHCO₃, with water and with brine, then dried (Na₂SO₄), filtered off and the solvent was evaporated under reduced pressure. The residue was purified by short open column chromatography (eluent: CH₂Cl₂/(CH₃OH/NH₃) 95/5). The product fractions were collected and the solvent was evaporated. Yield: 3.7 g of final compound 102.

Example B13

Preparation of Final Compounds 95

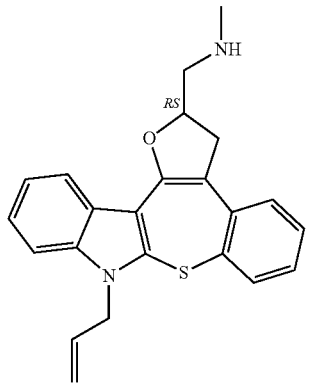

A mixture of intermediate compound 10 (prepared according to A4.c) (0.000212 mol), CH₃NH₂ (0.00212 mol) and CaO (q.s.) in THF (q.s) was heated in a high-pressure Parr vessel for 16 hours at 140° C. (oil bath temperature), then the suspension was filtered and the filtrate was evaporated under reduced pressure. The residue was purified by short open column chromatography (eluent: CH₂Cl₂/CH₃OH 98/2). The product fractions were collected and the solvent was evaporated. Yield: 0.072 g of final compound 95.

Example B14

Preparation of Final Compounds 131

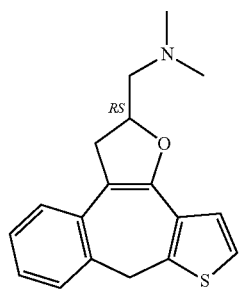

Dimethylamine (0.0010 mol) was added to a solution of intermediate compound 27 (prepared according to A7.b) (0.001 mol) in THF (5 mL) and the resultant reaction mixture was stirred and refluxed for 12 hours into a high-pressure Parr reaction vessel, then cooled and solvent was evaporated in vacuo. The residue was purified by column chromatography over silica gel (eluent: EtOAc/methanol 90/10). The product fractions were collected and the solvent was evaporated. Yield: 0.11 g of final compound 131 (39%; mp. 174-176° C.).

Example B15

Preparation of Final Compound 1

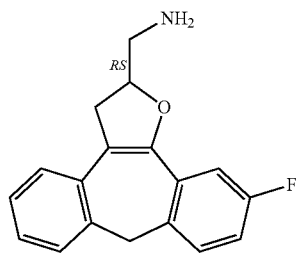

A mixture of intermediate compound 31 (1.13 g; 0.0037 mol), Pd/C 10% (catalytic) in Methanol (15 mL) and EtOAc (15 mL) was hydrogenated at rt under hydrogen pressure of 50 psi for 1 h. Then, the catalyst was filtered off through a celite pad and the filtrate was evaporated in vacuo. The resulting residue was purified by short open column chromatography (eluent: CH₂Cl₂, then CH₂Cl₂/MeOH(NH₃) 96:4). The product fractions were collected and vacuum evaporated to give 1 g of final compound 1 (Yield: 96%)

Example B16

Preparation of Final Compound 6

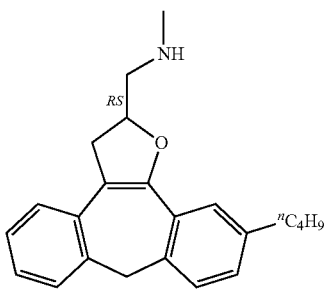

Reaction under nitrogen atmosphere. To a solution of final compound 5 (0.2 g; 0.56 mmol) in dry THF (20 mL) at −30° C., nButyllithium (1.6 M in hexanes) was dropwise added. The mixture was allowed to slowly warm to rt. Water was added and layers were separated. The organic phase was dried ($Na_2SO_4$) and vacuum concentrated, affording a residue that was purified by short open column chromatography. The product fractions were collected and vacuum evaporated to give final compound 6. (Yield: 10%)

Tables 1-5 list compounds of Formula (I), which were prepared according to one of the above examples. Table 5 shown LCMS data for a selected set of compounds.

TABLE 1

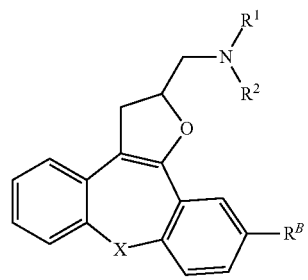

| Co. No | Ex. No. | $R^1$ | $R^2$ | X | $R^B$ | Physical data |
|---|---|---|---|---|---|---|
| 1 | B15 | H | H | $CH_2$ | F | RS-enantiomeric mixture |
| 144 | B11.a | H | $CH_3$ | $CH_2$ | F | RS-enantiomeric mixture |
| 2 | B11.a | H | $CH_3$ | $CH_2$ | F | RS-enantiomeric mixture; •oxalate |
| 3 | B1.a | H | $CH_3$ | $CH_2$ | F | R, •HCl; m.p. 244.9° C.; αD +75.55° (Na), c 0.54 |
| 4 | B1.a | H | $CH_3$ | $CH_2$ | F | S, •HCl; m.p. 249.2° C.; αD −75.92° (Na), c 0.54 |
| 139 | B1.b | H | $CH_3$ | $CH_2$ | F | R |
| 5 | B1.3 | H | $CH_3$ | $CH_2$ | Br | RS-enantiomeric mixture |
| 6 | B16 | H | $CH_3$ | $CH_2$ | nBu | RS-enantiomeric mixture |
| 7 | B1.b | H | $CH_3$ | >C(CH₃)< | H | 2RS,8RS |
| 8 | B1.b | H | $CH_3$ | >C(CH₃)< | F | 2RS,8RS |
| 9 | B1.b | H | $CH_3$ | >C(CH₃)< | H | 2SR,8SR; •HCl |
| 10 | B1.b | H | $CH_3$ | >C(CH₃)< | H | 2SR,8RS; •HCl |
| 11 | B1.b | H | $CH_3$ | >C=  | H | RS-enantiomeric mixture; •oxalate |
| 12 | B2.c | H | $CH_3$ | O | F | RS-enantiomeric mixture; •oxalate |
| 13 | B2.a | H | $CH_3$ | S | F | R*, •oxalate; m.p. 234.4° C.; αD free base +48.1° (Na), c 0.43 |
| 14 | B2a | H | $CH_3$ | S | F | S*, •oxalate; m.p. 231.5° C.; αD free base −50.0° (Na), c 0.33 |
| 30 | B2a | H | $CH_2CH_3$ | $CH_2$ | F | RS-enantiomeric mixture; •oxalate |
| 15 | B2a | H | $CH_2CH_3$ | $CH_2$ | F | R*, •oxalate ; m.p. 234.6° C.; αD free base −69.3° (Na), c 0.39 |
| 16 | B2a | H | $CH_2CH_3$ | $CH_2$ | F | S*, •oxalate; m.p. 240.7° C.; |

TABLE 1-continued

[Structure: tricyclic compound with N(R¹)(R²) group attached via CH₂ to dihydrofuran ring fused to dibenzo system with X bridge and R^B substituent]

| Co. No | Ex. No. | R¹ | R² | X | R^B | Physical data |
|---|---|---|---|---|---|---|
| 17 | B2a | H | CH₂CH₃ | CH₂ | Br | αD free base +74.5° (Na), c 0.44 RS-enantiomeric mixture |
| 18 | B2a | H | CH₂CH₃ | S | F | RS-enantiameric mixture; •oxalate; m.p. 240.7° C. |
| 19 | B2a | H | CH₂CH₂OH | CH₂ | F | RS-enantiomeric mixture; •oxalate; m.p. 209° C. |
| 20 | B2a | H | CH₂CH₂OH | CH₂ | Br | RS-enantiomeric mixture; m.p. 140.2° C. |
| 103 | B1.c | —H | phenyl | CH₂ | F | 2S |
| 104 | B1.c | —H | 4-hydroxyphenyl | CH₂ | F | 2S |
| 105 | B1.c | —H | 4-methoxyphenyl | CH₂ | F | 2S |
| 106 | B1.c | —H | 2-methoxyphenyl | CH₂ | F | 2S |
| 21 | B1.b | CH₃ | CH₃ | CH₂ | Br | RS-enantiomeric mixture |
| 22 | B5a | CH₃ | CH₃ | CH₂ | H | RS-enantiomeric mixture; •oxalate; m.p. 172.8° C. |
| 23 | B1a | CH₃ | CH₃ | CH₂ | H | R*, •oxalate; m.p. 185.7° C.; αD +39.3° (Na), c 0.44 |
| 24 | B1a | CH₃ | CH₃ | CH₂ | H | S*, •oxalate; m.p. 189.6; αD −39.5° (Na), c 0.55 |
| 101 | B5b | CH₃ | CH₃ | O | H | RS-enantiomeric mixture |
| 25 | B5b | CH₃ | CH₃ | O | H | RS-enantiomeric mixture; •oxalate |
| 26 | B2b | CH₃ | CH₃ | O | F | RS-enantiomeric mixture; •oxalate |
| 100 | B2b | CH₃ | CH₃ | O | Br | RS-enantiomeric mixture |
| 27 | B2b | CH₃ | CH₃ | O | Br | RS-enantiomeric mixture •oxalate |
| 28 | B2a | CH₃ | CH₃ | S | F | RS-enantiomeric mixture; •oxalate |
| 29 | B2a | CH₃ | CH₃ | N—CH₃ | H | RS-enantiomeric mixture; •oxalate |
| 142 | B8.a | —CH₃ | CH₂CN | CH₂ | F | 2R |
| 31 | B4 | CH₃ | CH₂CH₂OH | CH₂ | F | RS-enantiomeric mixture ; •oxalate |
| 32 | B1b | CH₃ | CH₂CH₂OH | O | F | RS-enantiomeric mixture; •trifluoroacetate |
| 107 | B9.b | —CH₃ | CH₂CO₂H | CH₂ | F | 2R; m.p. 194.7° C. |
| 108 | B9.b | —CH₃ | CH₂CH₂CO₂H | CH₂ | F | 2R |
| 109 | B9.b | —CH₃ | CH=CHCO₂H | CH₂ | F | 2R-(E) |

TABLE 1-continued

| Co. No | Ex. No. | R¹ | R² | X | R^B | Physical data |
|---|---|---|---|---|---|---|
| 145 | B9.a | —CH₃ | (E)-cinnamyl | CH₂ | F | 2R-(E) |
| 110 | B9.a | —CH₃ | (E)-cinnamyl | CH₂ | F | 2R-(E); (1:1)Hydrochloride; m.p. 136.8° C. |
| 111 | B10.b | —CH₃ | —CH₂C(O)OPh | CH₂ | F | 2R |
| 112 | B10.b | —CH₃ | —CH₂C(O)CH₂C(O)OMe | CH₂ | F | 2R |
| 143 | B9.a | —CH₃ | —CH₂C(O)OEt | CH₂ | F | 2R |
| 113 | B9.a | —CH₃ | —CH₂C(O)OEt | CH₂ | F | 2R (1:1)Hydrochloride; m.p. 99.3° C. |
| 146 | B9.a | —CH₃ | —CH₂C(O)Ph | CH₂ | F | 2R |
| 114 | B9.a | —CH₃ | —CH₂C(O)Ph | CH₂ | F | 2R; (1:1)Hydrochloride; m.p. 123.4° C. |
| 147 | B9.a | —CH₃ | —CH₂C(O)NH₂ | CH₂ | F | 2R |
| 115 | B9.a | —CH₃ | —CH₂C(O)NH₂ | CH₂ | F | 2R; (1:1)Hydrochloride; m.p. 225.3° C. |
| 148 | B9.d | —CH₃ | —CH₂C(O)NHCH₃ | CH₂ | F | 2R |

TABLE 1-continued
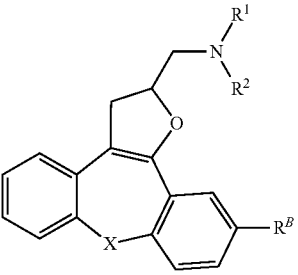
| Co. No | Ex. No. | R¹ | R² | X | R^B | Physical data |
|---|---|---|---|---|---|---|
| 116 | B9.d | —CH₃ | 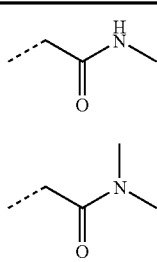 | CH₂ | F | 2R; (1:1)Hydrochoride; m.p. 120.8° C. |
| 149 | B9.a | —CH₃ | 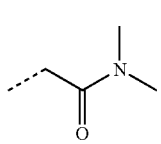 | CH₂ | F | 2R |
| 117 | B9.a | —CH₃ | 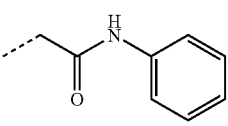 | CH₂ | F | 2R; (1:1)Hydrochoride; m.p. 145.2° C. |
| 150 | B9.d | —CH₃ | 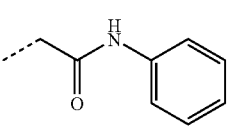 | CH₂ | F | 2R |
| 118 | B9.d | —CH₃ | 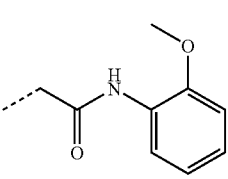 | CH₂ | F | 2R; (1:1)Hydrochoride; m.p. 181.3° C. |
| 120 | B9.d | —CH₃ | 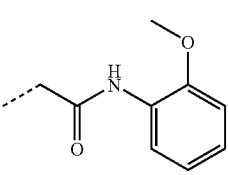 | CH₂ | F | 2R |
| 119 | B9.d | —CH₃ | 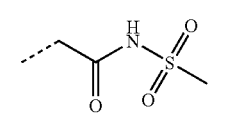 | CH₂ | F | 2R; (1:1)Hydrochoride; m.p. 129.9° C. |
| 120 | B9.c | —CH₃ | 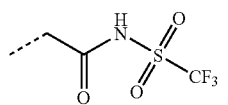 | CH₂ | F | 2R; m.p. 88.5° C. |
| 121 | B9.c | —CH₃ |  | CH₂ | F | 2R |

TABLE 1-continued
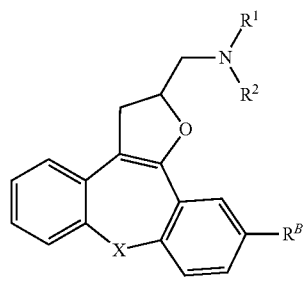
| Co. No | Ex. No. | R¹ | R² | X | R^B | Physical data |
|---|---|---|---|---|---|---|
| 122 | B9.c | —CH₃ | ⸺C(O)NHS(O)₂Ph | CH₂ | F | 2R; m.p. 156.1° C. |
| 123 | B9.d | —CH₃ | ⸺CH=CH-C(O)NHCH₃ | CH₂ | F | 2R-(E) |
| 124 | B10.a | —CH₃ | 3-succinimidyl | CH₂ | F | 2R-(3'RS) |
| 125 | B8.b | —CH₃ | CH₂-(1H-tetrazol-5-yl) | CH₂ | F | 2R |
| 126 | B10.b | —CH₃ | S(O)₂Et | CH₂ | F | 2R |
| 127 | B11.b | —CH₃ | S(O)₂Et | CH₂ | F | 2RS |
| 138 | B8.c | —CH₃ | C(=NH)NHCH₃ | CH₂ | F | 2R |

TABLE 2

| Co No | Ex. No | —NR¹R² | X | R^B | Physical data |
|---|---|---|---|---|---|
| 33 | B4 | (RS) pyrrolidine-3-OH | CH₂ | F | RS-enantiomeric mixture •oxalate |
| 34 | B4 | (RS) pyrrolidine-3-OH | S | F | RS-enantiomeric mixture •oxalate |
| 35 | B4 | (RS) pyrrolidine-3-N(CH₃)₂ | CH₂ | F | RS-enantiomeric mixture •oxalate |
| 36 | B4 | piperidine-4-OH | CH₂ | F | RS-enantiomeric mixture •oxalate |
| 37 | B4 | (RS) piperidine-3-OH | CH₂ | F | RS-enantiomeric mixture •oxalate |
| 38 | B4 | piperidine-4-CH₂CH₂OH | CH₂ | F | RS-enantiomeric mixture •oxalate |
| 39 | B4 | 1,4-dioxa-8-azaspiro[4.5]decane | CH₂ | F | RS-enantiameric mixture •oxalate |
| 40 | B4 | 6,7-dimethoxy-1,2,3,4-tetrahydroisoquinoline | CH₂ | F | RS-enantiomeric mixture •oxalate |
| 43 | B1.b | morpholine | CH₂ | F | RS-enantiomeric mixture •oxalate |
| 102 | B1.b | piperazine-NH | CH₂ | F | RS-enantiomeric mixture |

TABLE 2-continued

| Co No | Ex. No | —NR¹R² | X | R^B | Physical data |
|---|---|---|---|---|---|
| 41 | B4 | piperazine-N-CH₂CH₂OH | $CH_2$ | F | RS-enantiomeric mixture •oxalate |
| 42 | B1.b | piperazine-N-CH₂CH₂OH | S | F | RS-enantiomeric mixture •oxalate |
| 44 | B6a | piperazine-N-SO₂-CH₃ | $CH_2$ | F | RS-enantiomeric mixture •trifluoroacetate |
| 45 | B6a | piperazine-N-SO₂-CH₃ | O | F | RS-enantiomeric mixture •trifluoroacetate |
| 46 | B6a | piperazine-N-SO₂-CH₂CH₃ | $CH_2$ | F | RS-enantiomeric mixture •trifluoroacetate |
| 47 | B6a | piperazine-N-SO₂-CH₂CH₃ | O | F | RS-enantiomeric mixture •trifluoroacetate |
| 48 | B6a | piperazine-N-SO₂-phenyl | $CH_2$ | F | RS-enantiomeric mixture •trifluoroacetate |
| 49 | B6a | piperazine-N-SO₂-(4-methylphenyl) | $CH_2$ | F | RS-enantiomeric mixture •trifluoroacetate |
| 50 | B6a | piperazine-N-SO₂-(4-methylphenyl) | O | F | RS-enantiomeric mixture •trifluoroacetate |

TABLE 2-continued

| Co No | Ex. No | —NR¹R² | X | R$^B$ | Physical data |
|---|---|---|---|---|---|
| 51 | B6a | piperazine-N-SO₂-CH₂-phenyl | CH₂ | F | RS-enantiomeric mixture •trifluoroacetate |
| 52 | B6a | piperazine-N-SO₂-CH₂-phenyl | O | F | RS-enantiomeric mixture •trifluoroacetate |
| 53 | B6a | piperazine-N-C(O)-CH₃ | CH₂ | F | RS-enantiomeric mixture •trifluoroacetate |
| 54 | B6a | piperazine-N-C(O)-CH₃ | O | F | RS-enantiomeric mixture •trifluoroacetate |
| 55 | B6a | piperazine-N-C(O)-CH₂CH₂CH₃ | CH₂ | F | RS-enantiomeric mixture •trifluoroacetate |
| 56 | B6a | piperazine-N-C(O)-CH₂CH₂CH₃ | O | F | RS-enantiomeric mixture •trifluoroacetate |
| 57 | B6a | piperazine-N-C(O)-cyclopropyl | CH₂ | F | RS-enantiomeric mixture •trifluoroacetate |

TABLE 2-continued

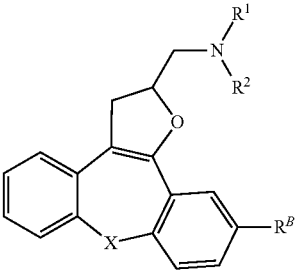

| Co No | Ex. No | —NR¹R² | X | R^B | Physical data |
|---|---|---|---|---|---|
| 58 | B6a | 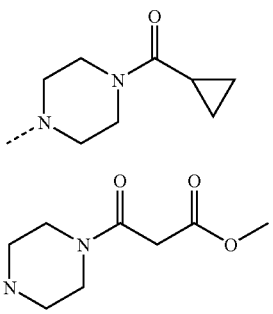 | O | F | RS-enantiomeric mixture •trifluoroacetate |
| 59 | B6a | 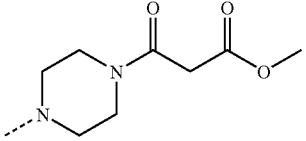 | CH₂ | F | RS-enantiomeric mixture •trifluoroacetate |
| 60 | B6a | 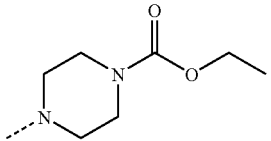 | O | F | RS-enantiomeric mixture •trifluoroacetate |
| 61 | B6a | 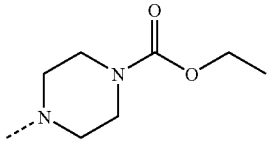 | CH₂ | F | RS-enantiomeric mixture •trifluoroacetate |
| 62 | B6a | 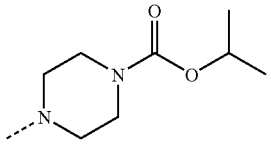 | O | F | RS-enantiomeric mixture •trifluoroacetate |
| 63 | B6a | 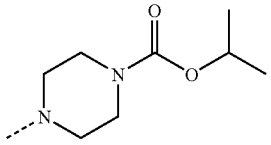 | CH₂ | F | RS-enantiomeric mixture •trifluoroacetate |
| 62 | B6a | 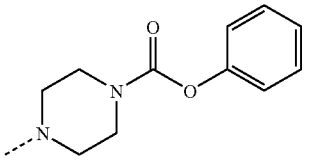 | O | F | RS-enantiomeric mixture •trifluoroacetate |
| 65 | B6a |  | CH₂ | F | RS-enantiomeric mixture •trifluoroacetate |

TABLE 2-continued

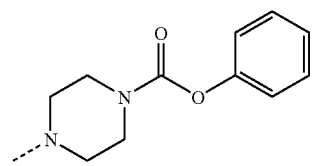

| Co No | Ex. No | —NR$^1$R$^2$ | X | R$^B$ | Physical data |
|---|---|---|---|---|---|
| 66 | B6a | 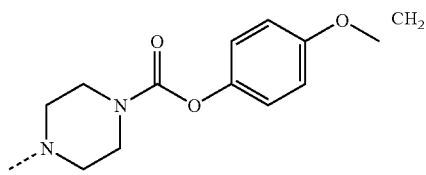 | O | F | RS-enantiomeric mixture •trifluoroacetate |
| 67 | B6a | 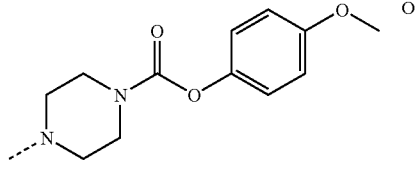 | CH$_2$ | F | RS-enantiomeric mixture •trifluoroacetate |
| 68 | B6a | 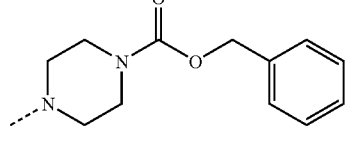 | O | F | RS-enantiomeric mixture •trifluoroacetate |
| 69 | B6a | 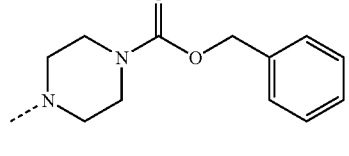 | CH$_2$ | F | RS-enantiomeric mixture •trifluoroacetate |
| 70 | B6a | 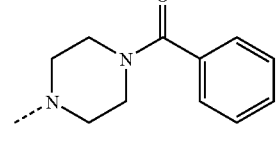 | O | F | RS-enantiomeric mixture •trifluoroacetate |
| 71 | B6a | 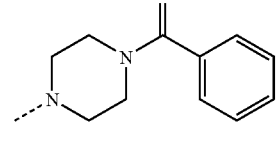 | CH$_2$ | F | RS-enantiomeric mixture •trifluoroacetate |
| 72 | B6a | | O | F | RS-enantiomeric mixture •trifluoroacetate |

TABLE 2-continued

| Co No | Ex. No | —NR¹R² | X | R^B | Physical data |
|---|---|---|---|---|---|
| 73 | B6a | piperazine-C(=O)-C6H4-OMe (4-methoxybenzoyl piperazine) | $CH_2$ | F | RS-enantiomeric mixture •trifluoroacetate |
| 74 | B6a | piperazine-C(=O)-C6H4-OMe (4-methoxybenzoyl piperazine) | O | F | RS-enautiomeric mixture •trifluoroacetate |
| 75 | B6a | piperazine-C(=O)-N(CH3)2 | $CH_2$ | F | RS-enantiomeric mixture •trifluoroacetate |
| 76 | B6a | piperazine-C(=O)-N(CH3)2 | O | F | RS-enantiomeric mixture •trifluoroacetate |
| 77 | B6b | piperazine-C(=O)-NH-propyl | $CH_2$ | F | RS-enantiomeric mixture •trifluoroacetate |
| 78 | B6b | piperazine-C(=O)-NH-propyl | O | F | RS-enantiomeric mixture •trifluoroacetate |
| 79 | B6b | piperazine-C(=O)-NH-cyclohexyl | $CH_2$ | F | RS-enantiomeric mixture •trifluoroacetate |

TABLE 2-continued

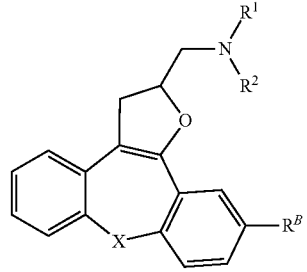

| Co No | Ex. No | —NR$^1$R$^2$ | X | R$^B$ | Physical data |
|---|---|---|---|---|---|
| 80 | B6b | 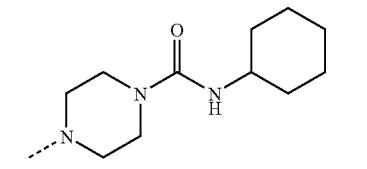 | O | F | RS-enantiomeric mixture •trifluoroacetate |
| 81 | B6b | 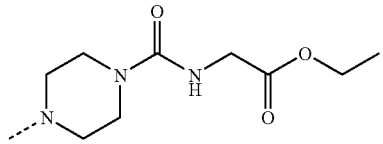 | CH$_2$ | F | RS-enantiomeric mixture •trifluoroacetate |
| 82 | B6b | 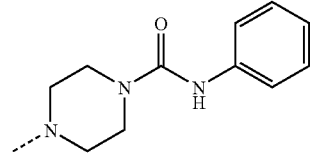 | O | F | RS-enantiomeric mixture •trifluoroacetate |
| 83 | B6b | 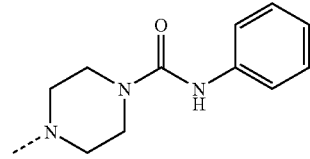 | CH$_2$ | F | RS-enantiomeric mixture •trifluoroacetate |
| 84 | B6b | 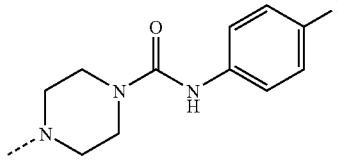 | O | F | RS-enantiomeric mixture •trifluoroacetate |
| 85 | B6b | 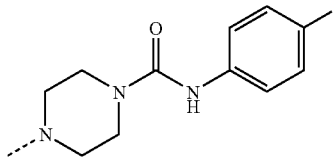 | CH$_2$ | F | RS-enantiomeric mixture •trifluoroacetate |
| 86 | B6b |  | O | F | RS-enantiomeric mixture •trifluoroacetate |

TABLE 2-continued

[Structure: tricyclic system with furan ring, bearing CH₂-N(R¹)(R²) substituent, with X linker and R^B substituent on aromatic ring]

| Co No | Ex. No | —NR¹R² | X | R^B | Physical data |
|---|---|---|---|---|---|
| 87 | B6b | piperazine-C(=O)-NH-CH₂-phenyl | CH₂ | F | RS-enantiomeric mixture •trifluoroacetate |
| 88 | B6b | piperazine-C(=O)-NH-CH₂-phenyl | O | F | RS-enantiomeric mixture •trifluoroacetate |
| 89 | B6b | piperazine-C(=O)-NH-(4-methoxyphenyl) | CH₂ | F | RS-enantiomeric mixture •trifluoroacetate |
| 90 | B6b | piperazine-C(=O)-NH-(4-methoxyphenyl) | O | F | RS-enantiomeric mixture •trifluoroacetate |

TABLE 3

[Structure: tricyclic system with furan ring, CH₂-N(R¹)(R²) substituent, X linker, and ring B fused]

| Co. No | Ex. No | R¹ | R² | X | B | Physical data |
|---|---|---|---|---|---|---|
| 131 | B14 | —CH₃ | —CH₃ | —CH₂— | thiophene (2,3-fused) | RS |

TABLE 3-continued
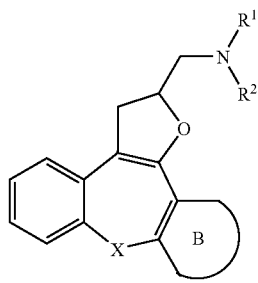
| Co. No | Ex. No | R¹ | R² | X | B | Physical data |
|---|---|---|---|---|---|---|
| 91 | B14 | H | CH₃ | N-benzyl | 3-pyridyl | RS-enantiomeric mixture |
| 92 | B3 | H | CH₃ | S | 1-methylindol-2,3-yl | RS-enantiomeric mixture • oxalate |
| 93 | B3 | H | CH₃ | S | 1-propylindol-2,3-yl | RS-enantiomeric mixture |
| 94 | B3 | CH₃ | CH₃ | S | 1-propylindol-2,3-yl | RS-enantiomeric mixture |
| 95 | B3 | H | CH₃ | S | 1-allylindol-2,3-yl | RS-enantiomeric mixture |

TABLE 4

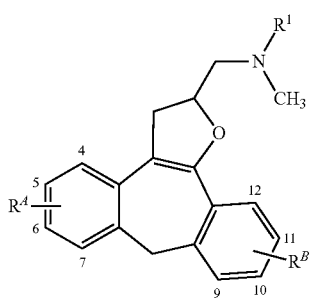

| Co. No | Ex. No | $R^A$ | $R^B$ | Physical data |
|---|---|---|---|---|
| 132 | B2.b | 4-F | H | RS-enantiomeric mixture; •oxalate; m.p. 230.5° C. |
| 96 | B2b | 5-F | H | RS-enantiomeric mixture |
| 133 | B2.b | 5-CN | H | RS-enantiomeric mixture; •oxalate; m.p. 187.6° C. |
| 97 | B2.b | 5-F | H | RS-enantiomeric mixture; •oxalate; m.p. 231.3° C. |
| 99 | B2.b | 5-F | 10-F | RS-enantiomeric mixture; •oxalate |
| 98 | B2.b | 6-F | 11-F | RS-enantiomeric mixture; •oxalate |
| 134 | B2.b | 6-F | H | RS-enantiomeric mixture; •oxalate; m.p. 214.7° C. |
| 135 | B2.b | H | 10-F | RS-enantiomeric mixture; •oxalate |
| 136 | B2.b | H | 12-F | RS-enantiomeric mixture; •oxalate |

TABLE 5

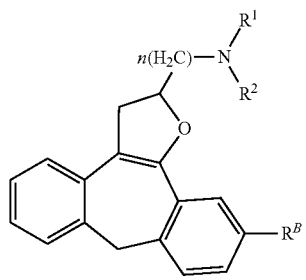

| Co. No | Ex. No | $R^1$ | $R^2$ | n | $R^B$ | Physical data |
|---|---|---|---|---|---|---|
| 140 | B7.a | H | H | 2 | F | 2RS enantiomeric mixture |
| 137 | B7.b | —CH₃ | —CH₃ | 2 | F | 2RS enantiomeric mixture; (1:1) •HCl; m.p. 201.1° C. |
| 141 | B7.b | —CH₃ | —CH₃ | 2 | F | 2RS enantiomeric mixture |

The LCMS data shown in Table 6 have been obtained by the following method:

The HPLC gradient was supplied by a HP 1100 from Agilent with a column heater set at 40° C. Flow from the column was passed through photodiode array (PDA) detector and then split to a Light Scattering detector (ELSD) and to a Waters-Micromass Time of Flight (ToF) mass spectrometer with an electrospray ionization source operated simultaneously in positive and negative ionization mode.

Reversed phase HPLC was carried out on a XDB-C18 cartridge (3.5 μm, 4.6×30 mm) from Agilent, with a flow rate of 1 ml/min. Three mobile phases (mobile phase A: 0.5 g/l ammoniumacetate solution, mobile phase B: acetonitrile; mobile phase C: methanol) were employed to run a gradient condition from 80% A, 10% B, 10% C to 50% B and 50% C in 6.0 min., to 100% B at 6.5 min., kept till 7.0 min and reequilibrated with 80% A, 10% B and 10% C at 7.6 min. that was kept till 9.0 min. An injection volume of 5 μL was used.

High Resolution Mass spectra were acquired by scanning from 100 to 750 in 1 s using a dwell time of 1 s. The capillary needle voltage was 3 kV and the source temperature was maintained at 140° C. Nitrogen was used as the nebulizer gas. Cone voltage was 30 V for both positive and negative ionization mode. Leucine-enkephaline was the reference used for the lock spray. Data acquisition was performed with a Waters-Micromass MassLynx-Openlynx data system. Unless otherwise specified, the parent peak mass corresponds to the free base+H⁺.

TABLE 6

Analytical data

| Co. No. | Retention time | Parent peak mass (ES+) | Remarks |
|---|---|---|---|
| 3 | 3.97 | 296 | |
| 5 | 4.54 | 356 | |
| 6 | 6.24 | 334 | |
| 7 | 4.03 | 292 | |
| 9 | 4.04 | 292 | |
| 12 | 3.86 | 298 | |
| 13 | 4.05 | 314 | Correspond to the free base |
| 14 | 4.18 | 314 | Correspond to the free base |
| 15 | 4.11 | 310 | |
| 16 | 4.08 | 310 | |
| 17 | 4.68 | 370 | |
| 19 | 4.11 | 326 | ES− = 324 |
| 20 | 4.64 | 386 | |
| 21 | 5.74 | 370 | |
| 25 | 4.85 | 294 | |
| 26 | 4.95 | 312 | |
| 27 | 5.79 | 372 | |
| 28 | 5.41 | 328 | |
| 29 | 4.51 | 307 | |
| 30 | 4.14 | 301 | |
| 31 | 5.03 | 340 | |
| 33 | 4.84 | 352 | |
| 34 | 4.93 | 370 | |
| 35 | 5.09 | 379 | |
| 36 | 5.05 | 366 | |
| 38 | 5.22 | 394 | |
| 39 | 5.92 | 408 | |
| 40 | 6.30 | 458 | |
| 41 | 4.85 | 395 | |
| 42 | 4.93 | 413 | |
| 43 | 5.68 | 352 | |
| 44 | 5.45 | 429 | |
| 45 | 5.19 | 431 | |
| 46 | 5.64 | 443 | |
| 47 | 5.40 | 445 | |
| 48 | 6.16 | 491 | |
| 49 | 6.36 | 385 | |
| 50 | 6.16 | 507 | |
| 51 | 6.08 | 505 | |
| 52 | 5.87 | 507 | |
| 53 | 5.28 | 393 | |
| 54 | 5.00 | 395 | |
| 55 | 5.84 | 421 | |
| 56 | 5.59 | 423 | |
| 57 | 5.66 | 419 | |
| 58 | 5.42 | 421 | |
| 59 | 5.33 | 451 | |
| 60 | 5.07 | 453 | |
| 61 | 6.11 | 423 | |
| 62 | 5.88 | 425 | |
| 63 | 6.32 | 437 | |
| 64 | 6.11 | 439 | |
| 65 | 6.35 | 471 | |
| 66 | 6.14 | 473 | |
| 67 | 6.32 | 501 | |
| 68 | 6.11 | 503 | |
| 69 | 6.47 | 485 | |
| 70 | 6.27 | 487 | |

TABLE 6-continued

Analytical data

| Co. No. | Retention time | Parent peak mass (ES+) | Remarks |
|---|---|---|---|
| 71 | 5.97 | 455 | |
| 72 | 5.74 | 457 | |
| 73 | 5.99 | 422 | |
| 74 | 5.76 | 487 | |
| 75 | 5.63 | 422 | |
| 76 | 5.37 | 424 | |
| 77 | 5.82 | 450 | |
| 78 | 5.60 | 452 | |
| 79 | 6.07 | 476 | |
| 80 | 5.85 | 478 | |
| 81 | 5.36 | 478 | |
| 82 | 5.40 | 482 | |
| 83 | 5.83 | 470 | ES− = 468 |
| 84 | 5.61 | 472 | |
| 85 | 5.86 | 488 | ES− = 486 |
| 87 | 5.81 | 484 | |
| 88 | 5.59 | 486 | |
| 89 | 5.75 | 500 | ES− = 498 |
| 90 | 5.55 | 502 | ES− = 500 |
| 92 | 4.51 | 349 | |
| 93 | 5.13 | 377 | |
| 94 | 6.22 | 391 | |
| 95 | 4.91 | 375 | |
| 98 | 4.01 | 314 | |
| 99 | 4.05 | 314 | |
| 103 | 6.35 | 358 | |
| 104 | 5.50 | 374 | |
| 105 | 6.21 | 388 | |
| 106 | 6.50 | 388 | |
| 107 | 3.71 | 354 | |
| 108 | 3.72 | 368 | |
| 109 | 3.89 | 380 | |
| 110 | 6.67 | 412 | |
| 111 | 6.16 | 416 | |
| 113 | 6.11 | 382 | |
| 114 | 6.34 | 414 | |
| 115 | 5.13 | 353 | |
| 116 | 5.36 | 367 | |
| 117 | 5.47 | 381 | |
| 118 | 6.13 | 429 | |
| 119 | 6.29 | 459 | |
| 120 | 3.52 | 431 | |
| 121 | 4.37 | 485 | |
| 122 | 4.09 | 493 | |
| 123 | 5.18 | 393 | |
| 124 | 5.11 | 393 | |
| 125 | 3.54 | 378 | |
| 126 | 5.45 | 388 | |
| 132 | 3.80 | 296 | |
| 133 | 3.46 | 303 | |
| 134 | 3.86 | 296 | |
| 135 | 3.93 | 296 | |
| 136 | 3.71 | 296 | |
| 137 | 4.78 | 324 | |

C. Pharmacological Example

Example C.1

In Vitro Binding Affinity for 5-$HT_{2A}$ and 5-$HT_{2C}$ Receptors

The interaction of the compounds of Formula (I) with 5-$HT_{2A}$ and 5-$HT_{2C}$ receptors was assessed in in vitro radioligand binding experiments. In general, a low concentration of a radioligand with a high binding affinity for the receptor is incubated with a sample of a tissue preparation enriched in a particular receptor (1 to 5 mg tissue) in a buffered medium (0.2 to 5 ml). During the incubation, the radioligands bind to the receptor. When equilibrium of binding is reached, the receptor bound radioactivity is separated from the non-bound radioactivity, and the receptor bound activity is counted. The interaction of the test compounds with the receptors is assessed in competition binding experiments. Various concentrations of the test compound are added to the incubation mixture containing the tissue preparation and the radioligand. Binding of the radioligand will be inhibited by the test compound in proportion to its binding affinity and its concentration. The affinities of the compounds for the 5-$HT_2$ receptors were measured by means of radioligand binding studies conducted with: (a) human cloned 5-$HT_{2A}$ receptor, expressed in L929 cells using [$^{125}$I]R91150 as radioligand and (b) human cloned 5-$HT_{2C}$ receptor, expressed in CHO cells using [$^3$H] mesulergine as radioligand.

Example C.2

In Vitro Determination of NET Reuptake Inhibition

Cortex from rat brain was collected and homogenised using an Ultra-Turrax T25 and a Dual homogeniser in ice-cold homogenising buffer containing Tris, NaCl and KCl (50 mM, 120 mM and 5 mM, respectively, pH 7.4) prior to dilution to an appropriate protein concentration optimised for specific and non-specific binding. Binding was performed with radioligand [$^3$H]Nixosetine (NEN, NET-1084, specific activity ~70 Ci/mmol) diluted in ice cold assay buffer containing Tris, NaCl and KCl (50 mM, 300 mM and 5 mM, respectively, pH 7.4). at a concentration of 20 nmol/L. Prepared radioligand (50 µl) was then incubated (60 min, 25° C.) with membrane preparations pre-diluted to an appropriate protein concentration (400 µl), and with 50 µL of either the 10% DMSO control, Mazindol ($10^{-6}$ mol/L final concentration), or compound of interest. Membrane-bound activity was detected by filtration through a Packard Filtermate harvester onto GF/B Unifilterplates, washed with ice-cold Tris-HCl buffer, containing NaCl and KCl (50 mM, 120 mM and 4 mM; pH 7.4; 6×0.5 ml). Filters were allowed to dry for 24 h before adding scintillation fluid. Scintillation fluid was allowed to saturate filters for 24 h before counting in a Topcount scintillation counter. Percentage specific bound and competition binding curves were calculated using S-Plus software (Insightful).

Example C.3

In Vitro Binding Affinity for Human $D2_L$ Receptor

Frozen membranes of human Dopamine $D2_L$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand [$^3$H]Spiperone (NEN, specific activity ~70 Ci/mmol) was diluted in assay buffer at a concentration of 2 nmol/L. Prepared radioligand (50 µl), along with 50 µl of either the 10% DMSO control, Butaclamol ($10^{-6}$ mol/l final concentration), or compound of interest, was then incubated (30 min, 37° C.) with 400 µl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful).

TABLE 7

Pharmacological data.

| Co. No. | h-5HT$_{2A}$ | h-5HT$_{2C}$ | h-D2L | NET Reuptake Inhibition |
|---|---|---|---|---|
| 34 | 9.9 | 9.3 | 8.0 | 6.3 |
| 14 | 9.6 | 9.7 | 7.6 | 8.6 |
| 38 | 9.5 | 8.9 | 8.7 | 5.4 |
| 18 | 9.4 | 8.9 | 7.8 | 8.5 |
| 28 | 9.4 | 9.3 | 7.9 | 8.3 |
| 4 | 9.3 | 9.2 | 7.2 | 8.0 |
| 36 | 9.2 | 9.2 | 8.2 | 5.2 |
| 2 | 9.2 | 9.0 | 7.1 | 7.8 |
| 5 | 9.1 | 9.1 | 7.5 | 6.6 |
| 33 | 9.1 | 9.1 | 7.4 | 5.9 |
| 37 | 9.0 | 8.7 | 7.7 | 5.4 |
| 1 | 8.8 | 9.1 | 6.5 | 6.5 |
| 19 | 8.8 | 9.0 | 7.2 | 7.4 |
| 123 | 8.7 | 8.7 | 7.3 | 6.7 |
| 89 | 8.7 | 8.5 | 7.4 | 5.2 |
| 59 | 8.7 | 8.3 | 6.5 | <5 |
| 31 | 8.6 | 8.8 | 7.4 | 7.4 |
| 30 | 8.6 | 8.8 | 7.3 | 8.1 |
| 134 | 8.5 | 8.8 | 6.2 | 6.0 |
| 114 | 8.5 | 8.8 | 6.1 | 7.0 |
| 125 | 8.5 | 8.6 | 5.9 | 7.1 |
| 13 | 8.5 | 8.4 | 6.7 | 8.2 |
| 85 | 8.5 | 8.3 | 7.0 | 5.3 |
| 42 | 8.5 | 8.0 | 8.3 | <5 |
| 57 | 8.4 | 7.7 | 6.5 | 5.3 |
| 73 | 8.4 | 7.5 | 7.1 | 5.6 |
| 22 | 8.4 | 8.4 | 6.2 | 7.1 |
| 77 | 8.4 | 8.1 | 6.9 | 5.1 |
| 53 | 8.4 | 8.1 | 6.7 | 5.7 |
| 55 | 8.4 | 8.0 | 6.5 | 5.6 |
| 41 | 8.3 | 7.9 | 8.0 | 5.1 |
| 135 | 8.3 | 8.6 | 5.5 | 6.2 |
| 71 | 8.2 | 7.8 | 6.9 | 5.3 |
| 40 | 8.2 | 8.6 | 7.3 | 5.4 |
| 90 | 8.2 | 7.5 | 6.3 | 5.7 |
| 3 | 8.2 | 8.2 | 6.4 | 7.8 |
| 27 | 8.1 | 8.6 | 7.3 | 6.3 |
| 95 | 8.1 | 8.2 | 6.4 | 6.8 |
| 117 | 8.0 | 8.7 | 5.6 | 6.1 |
| 61 | 8.0 | 7.7 | 6.7 | 5.5 |
| 132 | 8.0 | 8.4 | n.d. | 7.2 |
| 81 | 8.0 | 7.5 | 6.6 | <5 |
| 115 | 8.0 | 8.4 | 5.9 | 6.3 |
| 26 | 8.0 | 8.1 | 6.4 | 7.4 |
| 116 | 8.0 | 8.1 | 5.5 | 5.6 |
| 107 | 8.0 | 8.1 | 5.4 | 5.8 |
| 83 | 8.0 | 8.0 | 6.6 | 5.3 |
| 108 | 7.9 | 7.9 | 5.4 | 6.4 |
| 137 | 7.9 | 8.5 | 5.8 | 6.8 |
| 110 | 7.9 | 8.3 | 6.8 | 6.0 |
| 12 | 7.9 | 8.1 | 6.7 | 7.4 |
| 74 | 7.9 | 7.0 | 6.6 | 6.1 |
| 138 | 7.9 | 8.2 | 5.5 | 6.1 |
| 109 | 7.8 | 7.9 | 5.5 | 6.4 |
| 32 | 7.8 | 7.6 | 6.3 | 6.7 |
| 113 | 7.8 | 8.0 | 5.8 | 5.4 |
| 67 | 7.7 | 7.3 | 6.4 | 5.5 |
| 72 | 7.6 | 7.2 | 6.4 | 5.2 |
| 93 | 7.6 | 8.0 | 6.4 | 7.0 |
| 133 | 7.6 | n.d. | 5.69 | 6.5 |
| 119 | 7.5 | 7.6 | 5.1 | 5.3 |
| 92 | 7.5 | 7.3 | 6.3 | 6.6 |
| 84 | 7.5 | 7.3 | 6.0 | 5.8 |
| 6 | 7.5 | 8.1 | 6.6 | 5.1 |
| 8 | 7.5 | 8.0 | 5.7 | 7.4 |
| 54 | 7.5 | 7.0 | 5.8 | 5.8 |
| 11 | 7.4 | 7.7 | 5.8 | 7.6 |
| 82 | 7.4 | 6.8 | 5.8 | 5.7 |
| 131 | 7.4 | 8.1 | 6.7 | 6.1 |
| 124 | 7.4 | 7.2 | <5 | 5.2 |
| 80 | 7.4 | 7.1 | 6.0 | 5.8 |
| 79 | 7.4 | 7.1 | 5.8 | 5.1 |
| 65 | 7.3 | 6.9 | 6.0 | 5.5 |
| 76 | 7.3 | 6.8 | 6.6 | 5.7 |
| 7 | 7.3 | 7.7 | 5.7 | 7.2 |
| 75 | 7.3 | 6.5 | 6.1 | <5 |
| 118 | 7.3 | 8.0 | 6.1 | 5.2 |
| 25 | 7.2 | 7.7 | 5.9 | 6.6 |
| 68 | 7.2 | 6.6 | 6.1 | 5.8 |
| 51 | 7.1 | 6.7 | 7.0 | <5 |
| 62 | 7.1 | 6.7 | 6.2 | <5 |
| 78 | 7.1 | 7.3 | 5.9 | 5.9 |
| 45 | 7.1 | 7.0 | 6.1 | 6.0 |
| 52 | 7.0 | 6.7 | 6.8 | 6.0 |
| 64 | 7.0 | 6.6 | 6.2 | <5 |
| 9 | 7.0 | 7.3 | 5.4 | 7.1 |
| 56 | 7.0 | 7.0 | 5.9 | 5.8 |
| 126 | 6.9 | 8.4 | n.d. | 5.1 |
| 66 | 6.9 | 6.5 | 6.1 | 5.9 |
| 94 | 6.9 | 7.4 | 6.0 | 5.9 |
| 47 | 6.8 | 6.7 | 5.9 | 6.4 |
| 88 | 6.8 | 7.0 | 5.9 | 5.8 |
| 111 | 6.7 | 8.4 | n.d. | <5 |
| 50 | 6.7 | 6.5 | 5.7 | 5.8 |
| 112 | 6.7 | 7.2 | n.d. | 5.1 |
| 63 | 6.6 | 6.3 | 5.4 | <5 |
| 29 | 6.5 | 6.9 | 5.2 | 7.1 |
| 49 | 6.5 | 6.7 | 5.7 | <5 |
| 48 | 6.4 | 6.7 | 5.5 | <5 |
| 91 | 6.4 | 6.5 | 5.4 | 5.3 |
| 69 | 6.3 | 6.0 | 5.9 | 5.1 |
| 87 | 6.2 | 7.0 | 6.1 | 5.1 |
| 70 | 6.0 | 6.2 | 6.6 | <5 |
| 17 | n.d. | 8.9 | 7.6 | 7.0 |
| 24 | n.d. | 8.9 | 6.8 | 7.5 |
| 20 | n.d. | 8.8 | 7.5 | 6.3 |
| 16 | n.d. | 7.9 | 6.5 | 6.8 |
| 35 | n.d. | 7.8 | 7.4 | <5 |
| 99 | n.d. | 8.7 | 6.4 | 6.7 |
| 23 | n.d. | 7.8 | 5.8 | 6.2 |
| 136 | 7.6 | 8.7 | 5.8 | 7.0 |
| 43 | n.d. | 7.7 | 7.1 | 5.8 |
| 58 | n.d. | 6.8 | 5.8 | 5.8 |
| 46 | n.d. | 6.7 | 6.3 | <5 |
| 96 | n.d. | 8.5 | 6.1 | 7.1 |
| 10 | n.d. | 7.6 | 5.8 | 7.3 |
| 106 | 8.2 | 7.5 | <5 | <5 |
| 86 | n.d. | 7.4 | 6.6 | <5 |
| 21 | n.d. | 9.1 | 7.8 | 6.6 |
| 15 | n.d. | 9.1 | 7.4 | 8.5 |
| 39 | n.d. | 7.3 | 7.3 | <5 |
| 44 | n.d. | 7.3 | 6.8 | <5 |
| 60 | n.d. | 7.1 | 5.7 | 5.8 |
| 127 | 6.7 | 8.0 | <5 | <5 | n.d. = not determined

In Table 8 is demonstrated that the activity profile for 5-HT$_{2A/C}$, D2L and NET Reuptake inhibition is virtually unchanged while the complexity of the molecule has drastically been reduced.

TABLE 8

Comparative in vitro analysis of a preferred compound according to the invention with its corresponding prior art analogue.

| Co. No. | h-5HT$_{2A}$ | h-5HT$_{2C}$ | h-D2L | NET Reuptake Inhibition |
|---|---|---|---|---|
| 13 (Table 1, WO 99/19317 | 8.7 | 9.2 | 8 | 7.8 |
| 4 | 9.3 | 9.2 | 7.2 | 8.0 |

D. Composition Examples

"Active ingredient" (A.I.) as used throughout these examples relates to a compound of Formula (I), a pharmaceutically acceptable acid addition salt, a stereochemically isomeric form thereof or a N-oxide form thereof.

Example D.1

Oral Solution

Methyl 4-hydroxybenzoate (9 g) and propyl 4-hydroxybenzoate (1 g) were dissolved in boiling purified water (4 l). In 3 l of this solution were dissolved first 2,3-dihydroxybutanedioic acid (10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

Example D.2

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.
Coating To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

Example D.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and A.I. (4 g). The solution was cooled to room temperature and supplemented with water for injection q.s. ad 1000 ml, giving a solution comprising 4 mg/ml of A.I. The solution was sterilized by filtration and filled in sterile containers.

The invention claimed is:

1. A compound of Formula (I)

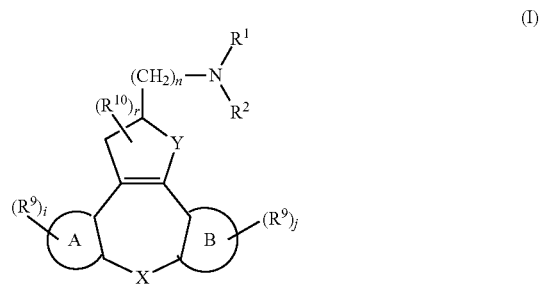

the pharmaceutically acceptable acid or base addition salts thereof, the stereochemically isomeric forms thereof, the N-oxide form thereof and prodrugs thereof, wherein:

n is an integer, equal to zero, 1, 2, 3, 4, 5 or 6;

i, j are integers, independently from each other, equal to zero, 1, 2, 3 or 4;

r is an integer, equal to zero, 1, 2 or 3;

$R^1$ and $R^2$ are, each independently from each other, selected from the group of hydrogen; alkyl; alkenyl; aryl; arylalkyl; arylalkenyl; alkyloxyalkyl; arylcarbonylalkyl; alkylcarbonyloxyalkyl; alkyloxycarbonylalkyl; alkylcarbonyl; arylcarbonyl; arylalkylcarbonyl; alkyloxycarbonyl; aryloxycarbonyl; alkyloxycarbonylalkylcarbonyl; mono- or di(alkyl)aminocarbonyl; mono- or di(aryl)aminocarbonyl; mono- or di(arylalkyl)aminocarbonyl; aminocarbonylalkyl; mono- or di(alkyloxycarbonylalkyl)aminocarbonyl; mono- or di(alkyl)aminocarbonylalkyl; mono- or di(aryl)aminocarbonylalkyl; mono- or di(alkyl)aminocarbonylalkenyl; mono- or di(alkylsulphonyl)-aminocarbonylalkyl; mono- or di(arylsulphonyl)aminocarbonylalkyl; alkylsulphonyl; arylsulphonyl; arylalkylsulphonyl; mono- or di(alkyl)aminothiocarbonyl; mono- or di(aryl)aminothiocarbonyl; mono- or di(arylalkyl)aminothiocarbonyl; mono-, di- or tri(alkyl)amidino; mono-, di- or tri(alkyl)amidinoalkyl; mono-, di- or tri(aryl)amidino and mono-, di- or tri(arylalkyl)amidino; pyrrolidinyl, optionally substituted with one or more oxo moieties; tetrazolylalkyl; or $R^1$ and $R^2$ taken together with the nitrogen atom to which they are attached may form a radical of Formula (a-1) to (a-7):

-continued

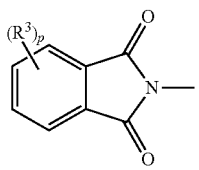 (a-2)

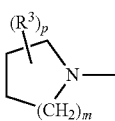 (a-3)

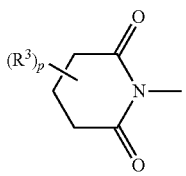 (a-4)

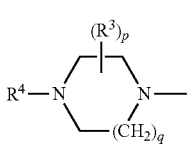 (a-5)

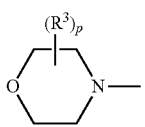 (a-6)

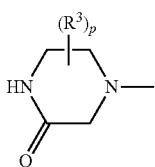 (a-7)

wherein:
P is an integer, equal to zero, 1, 2, 3 or 4;
q is an integer, equal to 1 or 2;
m is an integer, equal to zero, 1, 2 or 3;
each $R^3$ is, independently from each other, selected from the group of halo; hydroxy; alkyloxy; aryloxy; alkyl; aryl; alkylcarbonyl; alkyloxycarbonyl; arylcarbonyl; aryloxycarbonyl and mono- or di(alkyl)amino; or
two $R^3$-radicals may form together a bivalent radical of Formula —$CR^5R^5$—$CR^5R^5$—O— (b-1);

—O—$CR^5R^5$—$CR^5R^5$— (b-2);

—O—$CR^5R^5$—$CR^5R^5$—O— (b-3);

—O—$CR^5R^5$—$CR^5R^5$—$CR^5R^5$— (b-4);

—$CR^5R^5$—$CR^5R^5$—$CR^5R^5$—O— (b-5);

—O—$CR^5R^5$—$CR^5R^5$—$CR^5R^5$—O— (b-6);

—O—$CR^5R^5$—$CR^5R^5$—$CR^5R^5$—$CR^5R^5$ (b-7);

—$CR^5R^5$—$CR^5R^5$—$CR^5R^5$—$CR^5R^5$—O— (b-8); and

—O—$CR^5R^5$—$CR^5R^5$—$CR^5R^5$—O— (b-9);

wherein $R^5$ is selected from the group of hydrogen; halo; hydroxy; alkyloxy and alkyl;

$R^4$ is selected from the group of hydrogen; alkyl; alkylcarbonyl; arylcarbonyl; alkyloxycarbonyl; aryloxycarbonyl; arylalkylcarbonyl; alkyloxycarbonylalkylcarbonyl; arylalkyl; alkyloxyalkyl; alkylcarbonyloxyalkyl; alkyloxycarbonylalkyl; mono- or di(alkyl)aminocarbonyl; mono- or di(aryl)aminocarbonyl; mono- or di(arylalkyl)aminocarbonyl; mono- or di(alkyloxycarbonylalkyl)-aminocarbonyl; alkylsulphonyl; arylsulphonyl; arylalkylsulphonyl; mono- or di(alkyl)aminothiocarbonyl; mono- or di(aryl)aminothiocarbonyl; mono- or di(arylalkyl)aminothiocarbonyl; mono-, di- or tri(alkyl)amidino; mono-, di- or tri(aryl)amidino and mono-, di- or tri(arylalkyl)amidino;

A and B are, each independently from each other, aryl or an heteroaryl radical selected from the group of; thienyl; pyridinyl; and indolyl;

each $R^9$ is, independently from each other, selected from the group of hydrogen; halo; cyano; hydroxy; carboxyl; nitro; amino; mono- or di(alkyl)amino; alkylcarbonylamino; aminosulfonyl; mono- or di(alkyl)aminosulfonyl; alkyl; alkenyl; alkyloxy; alkylcarbonyl and alkyloxycarbonyl;

$R^{10}$ is selected from the group of hydrogen; alkyl; halo and cyano;

Y is O;

X is $CR^6R^7$; wherein
$R^6$ and $R^7$ each independently from each other, are selected from the group of hydrogen; hydroxy; alkyl and alkyloxy; or
$R^6$ and $R^7$ taken together may form a radical selected from the group of methylene (=$CH_2$); mono- or di(cyano)methylene; a bivalent radical of Formula —$(CH_2)_2$—, —$(CH_2)_3$—, —$(CH_2)_4$—, —$(CH_2)_5$—, —O—$(CH_2)_2$—O—, —O—$(CH_2)_3$O—; or, together with the carbon atom to which they are attached, a carbonyl;

aryl is phenyl, optionally substituted with 1, 2 or 3 substituents independently from each other, selected from the group of halo, hydroxy, alkyloxy and alkyl;

alkyl is a straight or branched saturated hydrocarbon radical having from 1 to 6 carbon atoms; or a cyclic saturated hydrocarbon radical having from 3 to 6 carbon atoms; each radical optionally substituted with one or more radicals selected from the group of halo, cyano, oxo, hydroxy, formyl, carboxyl and amino;

alkenyl is a straight or branched unsaturated hydrocarbon radical having from 4-2 to 6 carbon atoms; or a cyclic unsaturated hydrocarbon radical having from 3 to 6 carbon atoms; each radical optionally substituted with one or more radicals selected from the group of halo, cyano, oxo, hydroxy, formyl, carboxyl or amino radicals; and halo is fluoro, chloro, bromo or iodo.

2. A compound according to claim 1, wherein
n is equal to 1 or 2;
i, j are, independently from each other, equal to zero or 1;
r is equal to 0 or 1;
$R^1$ and $R^2$ are, each independently from each other, hydrogen; alkyl; alkenyl; aryl; arylalkenyl; arylcarbonylalkyl; alkyloxycarbonylalkyl; aryloxycarbonyl; alkyloxycarbonylalkylcarbonyl; aminocarbonylalkyl; mono- or di(alkyl)aminocarbonylalkyl; mono- or di(aryl)aminocarbonylalkyl; mono- or di(alkyl)aminocarbonylalkenyl; mono- or di(alkylsulphonyl)-aminocarbonylalkyl; mono- or di(arylsulphonyl)aminocarbonylalkyl; alkylsulphonyl; mono-, di- or tri(alkyl)amidinoalkyl; pyrrolidinyl, optionally substituted with one or more oxo moieties; tetrazolylalkyl; or $R^1$ and $R^2$ taken together with the nitrogen atom to which they are attached may form a radical of Formula (a-1), (a-3), (a-5), (a-6) or (a-7) wherein:

P is equal to zero, 1 or 2;

q is equal to 1;

m is equal to 1 or 2;

each $R^3$ is, independently from each other, selected from the group of hydroxy; alkyloxy; alkyl; and mono- or di(alkyl)amino; or two $R^3$-radicals may form together a bivalent radical of Formula (b-3) wherein $R^5$ is hydrogen;

$R^4$ is selected from the group of alkyl; alkylcarbonyl; arylcarbonyl; alkyloxycarbonyl; aryloxycarbonyl; arylalkylcarbonyl; alkyloxycarbonylalkylcarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl and arylalkylsulphonyl;

A and B are, each independently from each other, aryl or an heteroaryl radical selected from the group of thienyl; pyridinyl and indolyl;

each $R^9$ is, independently from each other, selected from the group of hydrogen;

halo; cyano; alkyl and alkenyl;

$R^{10}$ is hydrogen;

Y is O;

X is $CR^6R^7$; wherein $R^6$ and $R^7$ each independently from each other are selected from the group of hydrogen and alkyl; or $R^6$ and $R^7$ taken together may form the radical methylene ($=CH_2$); or, together with the carbon atom to which they are attached, a carbonyl;

aryl is phenyl, optionally substituted with 1 substituent selected from the group of halo, hydroxy, alkyloxy and alkyl;

alkyl is a straight saturated hydrocarbon radical having from 1 to 6 carbon atoms, optionally substituted with one or more hydroxy, cyano or carboxyl radicals;

alkenyl is a straight unsaturated hydrocarbon radical having from 4-2 to 6 carbon atoms; and halo is fluoro, chloro or bromo.

3. A compound according to claim 1 wherein n is equal to 1;

i is equal to 0;

j is equal to 1;

r is equal to 0;

$R^1$ and $R^2$ are, each independently from each other, hydrogen or methyl

A and B are phenyl;

$R^9$ is halo;

$R^{10}$ is hydrogen;

Y is O;

X is $CH_2$ and halo is fluoro, chloro or bromo.

4. A pharmaceutical composition comprising a pharmaceutically acceptable carrier and, as active ingredient, a therapeutically effective amount of a compound claim 1.

5. A process for the preparation of a composition as claimed in claim 4, characterized in that a pharmaceutically acceptable carrier is intimately mixed with a therapeutically effective amount of a compound of claim 1.

* * * * *